(12) United States Patent
Kim et al.

(10) Patent No.: US 12,318,402 B2
(45) Date of Patent: Jun. 3, 2025

(54) COMPOSITION FOR TREATING OR PREVENTING COLITIS BY NAMPT METABOLIC REGULATION

(71) Applicant: AJOU UNIVERSITY INDUSTRY-ACADEMIC COOPERATION FOUNDATION, Suwon-si (KR)

(72) Inventors: You-Sun Kim, Suwon-si (KR); Sun Mi Hong, Suwon-si (KR); A-Yeon Lee, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 257 days.

(21) Appl. No.: 18/086,971

(22) Filed: Dec. 22, 2022

(65) Prior Publication Data

US 2023/0285433 A1    Sep. 14, 2023

(30) Foreign Application Priority Data

Dec. 22, 2021 (KR) .......................... 10-2021-0184803
Apr. 19, 2022 (KR) .......................... 10-2022-0047932

(51) Int. Cl.
*A61K 31/706* (2006.01)
*A61P 29/00* (2006.01)

(52) U.S. Cl.
CPC ............ *A61K 31/706* (2013.01); *A61P 29/00* (2018.01)

(58) Field of Classification Search
CPC ............................... A61K 31/706; A61P 29/00
See application file for complete search history.

(56) References Cited

U.S. PATENT DOCUMENTS

2015/0265642 A1*  9/2015  Sinclair .................. A61P 25/28
                                                                424/94.5

FOREIGN PATENT DOCUMENTS

KR     10-2021-0091244 A      7/2021

OTHER PUBLICATIONS

Stromsdorfer, K. L., Yamaguchi, S., Yoon, M. J., Moseley, A. C., Franczyk, M. P., Kelly, S. C., . . . & Yoshino, J. (2016). NAMPT-mediated NAD+ biosynthesis in adipocytes regulates adipose tissue function and multi-organ insulin sensitivity in mice. Cell reports, 16(7), 1851-1860. (Year: 2016).*
Gerner, R. R., Klepsch, V., Macheiner, S., Arnhard, K., Adolph, T. E., Grander, C., . . . & Moschen, A. R. (2018). NAD metabolism fuels human and mouse intestinal inflammation. Gut, 67(10), 1813-1823. (Year: 2018).*

(Continued)

*Primary Examiner* — Scarlett Y Goon
*Assistant Examiner* — David H Cho
(74) *Attorney, Agent, or Firm* — NSIP Law

(57) ABSTRACT

The present disclosure relates to a pharmaceutical composition for treating or preventing inflammatory diseases including nicotinamide mononucleotide (NMN) as an active ingredient. When NAMPT was knocked out, removal of dead cells for tissue repair was failed, which leads to a significant increase in susceptibility to colitis, whereby systemic administration of NMN to supply NAD$^+$ can effectively suppress inflammatory severity, making it a potential therapeutic strategy for managing inflammatory diseases.

6 Claims, 57 Drawing Sheets

(56) References Cited

OTHER PUBLICATIONS

Harlan, B. A. et al. (2016). Enhancing NAD+ salvage pathway reverts the toxicity of primary astrocytes expressing amyotrophic lateral sclerosis-linked mutant superoxide dismutase 1 (SOD1). Journal of Biological Chemistry, 291(20), 10836-108 (Year: 2016).*

She, J., Sheng, R., & Qin, Z. H. (2021). Pharmacology and potential implications of nicotinamide adenine dinucleotide precursors. Aging and disease, 12(8), 1879. (Year: 2021).*

Donath, M. Y., & Shoelson, S. E. (2011). Type 2 diabetes as an inflammatory disease. Nature reviews immunology, 11(2), 98-107. (Year: 2011).*

Na, Yi Rang, et al. "Macrophages in intestinal inflammation and resolution: a potential therapeutic target in IBD." *Nature Reviews Gastroenterology & Hepatology* 16.9 (2019): 531-543.

Watanabe, Satoshi, et al. "The role of macrophages in the resolution of inflammation." *The Journal of clinical investigation* 129.7 (2019): 2619-2628.

Hine, Ashley M., and P'ng Loke. "Intestinal macrophages in resolving inflammation." *The Journal of Immunology* 203.3 (2019): 593-599.

Koo, Sue-jie, and Nisha J. Garg. "Metabolic programming of macrophage functions and pathogens control." *Redox biology* 24 (2019): 101198.

Rogler, Gerhard. "Resolution of inflammation in inflammatory bowel disease." *The Lancet Gastroenterology & Hepatology* 2.7 (2017): 521-530.

Peters, Lauren A., et al. "A functional genomics predictive network model identifies regulators of inflammatory bowel disease." *Nature genetics* 49.10 (2017): 1437-1449.

Garten, Antje, et al. "Nampt: linking NAD biology, metabolism and cancer." *Trends in Endocrinology & Metabolism* 20.3 (2009): 130-138.

Navas, Lola E., and Amancio Carnero. "NAD+ metabolism, stemness, the immune response, and cancer." *Signal Transduction and Targeted Therapy* 6.1 (2021): 1-20.

Chiarugi, Alberto, et al. "The NAD metabolome—a key determinant of cancer cell biology." *Nature Reviews Cancer* 12.11 (2012): 741-752.

Garten, Antje, et al. "Physiological and pathophysiological roles of NAMPT and NAD metabolism." *Nature Reviews Endocrinology* 11.9 (2015): 535-546.

Galli, Ubaldina, et al. "Recent advances in NAMPT inhibitors: a novel immunotherapic strategy." *Frontiers in Pharmacology* 11 (2020): 656.

Audrito, Valentina, Vincenzo Gianluca Messana, and Silvia Deaglio. "NAMPT and NAPRT: two metabolic enzymes with key roles in inflammation." *Frontiers in oncology* 10 (2020): 358.

Burczynski, Michael E., et al. "Molecular classification of Crohn's disease and ulcerative colitis patients using transcriptional profiles in peripheral blood mononuclear cells." *The journal of molecular diagnostics* 8.1 (2006): 51-61.

Gerner, Romana R., et al. "NAD metabolism fuels human and mouse intestinal inflammation." *Gut* 67.10 (2018): 1813-1823.

Ortega-Gómez, Almudena, Mauro Perretti, and Oliver Soehnlein. "Resolution of inflammation: an integrated view." *EMBO molecular medicine* 5.5 (2013): 661-674.

Zhu, Wei, et al. "Disequilibrium of M1 and M2 macrophages correlates with the development of experimental inflammatory bowel diseases." *Immunological investigations* 43.7 (2014): 638-652.

Isidro, Raymond A., and Caroline B. Appleyard. "Colonic macrophage polarization in homeostasis, inflammation, and cancer." *American Journal of Physiology—Gastrointestinal and Liver Physiology* 311.1 (2016): G59-G73.

Kawasaki, Takumi, and Taro Kawai. "Toll-like receptor signaling pathways." *Frontiers in immunology* (2014): 461.

Kourtzelis, Ioannis, George Hajishengallis, and Triantafyllos Chavakis. "Phagocytosis of apoptotic cells in resolution of inflammation." *Frontiers in Immunology* 11 (2020): 553.

Lee, Chang Sup, et al. "Boosting apoptotic cell clearance by colonic epithelial cells attenuates inflammation in vivo." *Immunity* 44.4 (2016): 807-820.

Sareila, Outi, et al. "Nox2 complex-derived ROS as immune regulators." *Antioxidants & redox signaling* 15.8 (2011): 2197-2208.

Hong, S. M., et al. "NAMPT suppresses glucose deprivation-induced oxidative stress by increasing NADPH levels in breast cancer." *Oncogene* 35.27 (2016): 3544-3554.

Benito-Martin, Alberto, et al. "Endogenous NAMPT dampens chemokine expression and apoptotic responses in stressed tubular cells." *Biochimica et Biophysica Acta (BBA)—Molecular Basis of Disease* 1842.2 (2014): 293-303.

Viola, Antonella, et al. "The metabolic signature of macrophage responses." *Frontiers in immunology* 10 (2019): 1462.

Yen, Wel-Chen, et al. "Impaired inflammasome activation and bacterial clearance in G6PD deficiency due to defective NOX/p38 MAPK/AP-1 redox signaling." *Redox biology* 28 (2020): 101363.

Rosenzweig, S. D. "Inflammatory manifestations in chronic granulomatous disease (CGD)." *Journal of Clinical Immunology* 28.1 (2008): 67-72.

Aviello, Gabriella, and Ulla G. Knaus. "NADPH oxidases and ROS signaling in the gastrointestinal tract." *Mucosal immunology* 11.4 (2018): 1011-1023.

Carter, Martyn J., Alan J. Lobo, and Simon PL Travis. "Guidelines for the management of inflammatory bowel disease in adults." *Gut* 53.suppl 5 (2004): v1-v16.

Yoshino, Jun, Joseph A. Baur, and Shin-ichiro Imai. "NAD+ intermediates: the biology and therapeutic potential of NMN and NR." *Cell metabolism* 27.3 (2018): 513-528.

Uddin, Golam Mezbah, et al. "Nicotinamide mononucleotide (NMN) supplementation ameliorates the impact of maternal obesity in mice: comparison with exercise." *Scientific Reports* 7.1 (2017): 1-11.

Martin, Angelical S., et al. "Nicotinamide mononucleotide requires SIRT3 to improve cardiac function and bioenergetics in a Friedreich's ataxia cardiomyopathy model." *JCI insight* 2.14 (2017).

Yao, Zhiwen, et al. "Nicotinamide mononucleotide inhibits JNK activation to reverse Alzheimer disease." *Neuroscience letters* 647 (2017): 133-140.

Aran, Dvir, Zicheng Hu, and Atul J. Butte. "xCell: digitally portraying the tissue cellular heterogeneity landscape." *Genome biology* 18.1 (2017): 1-14.

Zhou, Xin, et al. "YAP aggravates inflammatory bowel disease by regulating M1/M2 macrophage polarization and gut microbial homeostasis." *Cell Reports* 27.4 (2019): 1176-1189.

Bauché, David, et al. "LAG3+ regulatory T cells restrain interleukin-23-producing CX3CR1+ gut-resident macrophages during group 3 innate lymphoid cell-driven colitis." *Immunity* 49.2 (2018): 342-352.

Moriwaki, Kenta, et al. "The necroptosis adaptor RIPK3 promotes injury-induced cytokine expression and tissue repair." *Immunity* 41.4 (2014): 567-578.

De Picciotto, Natalie E., et al., "Nicotinamide Mononucleotide Supplementation Reverses Vascular Dysfunction and Oxidative Stress with Aging in Mice", Aging Cell, 2016, (p. 522-530).

Deng, Xiujun, et al. "Nicotinamide Mononucleotide (NMN) Protects bEnd.3 Cells Against H2O2-Induced Damage via NAMPT and the NF-κB p65 Signalling Pathway", FEBS Open Bio, 2021, (p. 866-879).

* cited by examiner

COMPOSITION FOR TREATING OR PREVENTING COLITIS BY NAMPT METABOLIC REGULATION

CROSS REFERENCE TO RELATED APPLICATIONS

This application claims the benefit of Korean Patent Application No. 10-2021-0184803 filed on Dec. 22, 2021, and No. 10-2022-0047932 filed on Apr. 19, 2022, in the Korean Intellectual Property Office, the entire disclosure of which is incorporated herein by reference for all purposes.

FIELD OF INVENTION

The present disclosure provides a composition for treating or preventing inflammatory bowel disease by regulating nicotinamide phosphoribosyltransferase (NAMPT) metabolism.

DESCRIPTION OF RELATED ART

Inflammation is a series of bodily processes that include activation steps designed to enable the rapid and powerful immune response needed to eliminate invading pathogens, followed by a gradual resolution phase. The resolution phase of inflammation is an active process controlled by the accumulation of activated macrophages with the ability to promote inflammation resolution for rapid return to homeostasis. Intestinal macrophages are important components for the fine-tuning of the mucosal immune system and play a key role in the innate immune response, where intestinal macrophages contribute to the production of cytokines, growth factors, and lipid mediators. It also functions to eliminate pathogens, bacterial wall components, and dead cells. Failure to build a strong protective response to pathogens during the resolution phase of inflammation may lead to persistent and excessive inflammation, which is often observed in the pathogenesis of inflammatory bowel diseases (IBD). Recent whole-genome association studies have identified a key driver gene for macrophages in IBD, and accumulating evidence supports the notion that expressing a pro-inflammatory phenotype in macrophages could be a novel therapeutic approach to modulate intestinal inflammation and restore tissue function.

Nicotinamide phosphoribosyltransferase (NAMPT) is an enzyme that induces nicotinamide mononucleotide (NMN) synthesis from nicotinamide (NAM) and 5'phosphoribosyl-1'-pyrophosphate (PRPP), and plays an important role in the cyclic biosynthetic pathway of nicotinamide adenine dinucleotide ($NAD^+$). $NAD^+$ is essential for maintaining cellular energy through redox reactions and has evolved as a substrate for $NAD^+$ cleavage enzymes such as poly(ADP-ribose) polymerases, sirtuins (SIRTS) and cADP-ribose synthase (e.g., CD38/CD157). $NAD^+$ is produced by two distinct biosynthetic pathways, salvage and de novo synthesis pathways. As a rate-limiting enzyme in the $NAD^+$ salvage pathway, NAMPT is biologically indispensable and has been linked to various inflammatory diseases such as rheumatoid arthritis, diabetes and sepsis. However, the role of NAMPT in inflammatory macrophages is not yet fully understood. Therefore, new treatment strategies through the activation of the NAMPT-dependent $NAD^+$ biosynthetic pathway for inflammatory diseases are continuously being studied.

PRIOR ART DOCUMENT

Patent Document

Patent Document 1. Korean Patent Application Publication No. 10-2021-0091244.

SUMMARY

Problem to be Solved by Invention

An object of the present disclosure is to provide a pharmaceutical composition for treating or preventing inflammatory diseases including nicotinamide mononucleotide (NMN) as an active ingredient.

Another object of the present disclosure is to provide a health functional food composition for improving or preventing inflammatory diseases including NMN as an active ingredient.

Another object of the present disclosure is to provide a reagent composition for increasing the expression of nicotinamide adenine dinucleotide phosphate (NADPH) including NMN as an active ingredient.

Means for Solving the Problem

In order to achieve the above object, the present disclosure provides a pharmaceutical composition for treating or preventing an inflammatory disease, including nicotinamide mononucleotide (NMN) as an active ingredient, wherein the inflammatory disease is caused by nicotinamide phosphoribosyltransferase (NAMPT) protein knock out.

In addition, the present disclosure provides a health functional food composition for improving or preventing an inflammatory disease, including NMN as an active ingredient, wherein the inflammatory disease is caused by NAMPT protein knock out.

In addition, the present disclosure provides a reagent composition for increasing expression of NADPH including NMN as an active ingredient.

Effects of Invention

The present disclosure relates to a pharmaceutical composition for treating or preventing inflammatory diseases including NMN as an active ingredient, and through administration of NMN into the human body, activation of the NAMPT-dependent $NAD^+$ biosynthetic pathway reduces the severity of inflammatory diseases, so it may be used as a medicine or treatment method for patients with inflammatory diseases caused by NAMPT knock out.

DETAILED DESCRIPTION

Figure 1A:
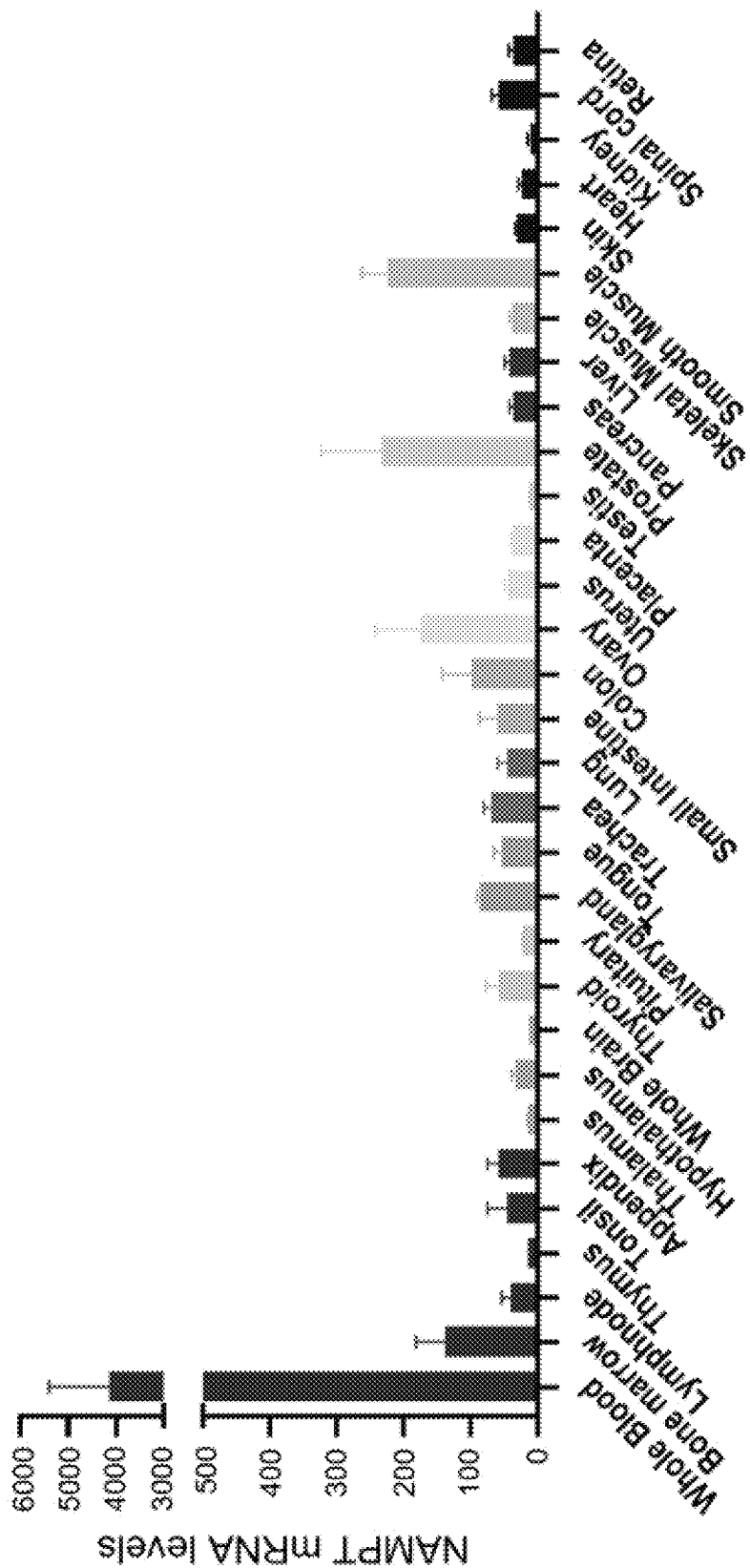
FIGS. 1A to 1F show a test for confirming changes in nicotinamide phosphoribosyltransferase (NAMPT) expression patterns in inflamed tissues and cells.

Hereinafter, the present disclosure will be described in more detail.

Knock out of NAMPT in macrophages may lead to a significant increase in sensitivity to inflammatory diseases, and the present inventor has completed the present disclosure to treat and prevent inflammatory diseases by activating the NAMPT-dependent $NAD^+$ biosynthetic pathway using NMN.

The present disclosure provides a pharmaceutical composition for treating or preventing inflammatory diseases including nicotinamide mononucleotide (NMN) as an active ingredient.

The inflammatory disease may be any one selected from the group consisting of inflammatory bowel disease (IBD), dermatitis, allergy, atopy, conjunctivitis, periodontitis, rhinitis, otitis media, sore throat, tonsillitis, pneumonia, gastric ulcer, gastritis, Crohn's disease, ulcerative colitis, ankylosing spondylitis, psoriatic arthritis, osteoarthritis, rheumatoid arthritis, periarthritis, tendonitis, tenosynovitis, peritendinitis, myositis, hepatitis, cystitis, nephritis, or sjogren's syndrome, but is not limited thereto.

The NAMPT protein knock out may be a knock out of NAMPT in macrophages.

The pharmaceutical composition may increase nicotinamide adenine dinucleotide phosphate (NADPH) expression.

The pharmaceutical composition may be administrated to a patient with low expression level or no expression of NAMPT protein in macrophages.

In another embodiment of the present disclosure, the pharmaceutical composition may include one or more additives selected from the group consisting of appropriate carriers, excipients, disintegrants, sweeteners, coating agents, swelling agents, lubricants, glidants, flavoring agents, antioxidants, buffers, bacteriostatic agents, diluents, dispersants, surfactants, binders and lubricants commonly used in the preparation of pharmaceutical compositions.

Specifically, as for the carriers, excipients and diluents, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil may be used. A solid formulation for oral administration includes tablets, pills, powders, granules, capsules, etc., and such a solid formulation may be prepared by mixing the composition with at least one or more excipients, for example, starch, calcium carbonate, sucrose or lactose, gelatin, and the like. In addition to simple excipients, lubricants such as magnesium styrrate and talc may also be used. A liquid formulation for oral administration include suspensions, oral liquids, emulsions, syrups, and the like, and various excipients such as wetting agents, sweeteners, aromatics, and preservatives may be included in addition to commonly used simple diluents such as water and liquid paraffin. A formulation for parenteral administration include sterilized aqueous solutions, non-aqueous solvents, suspensions, emulsions, lyophilized formulations, suppositories, and the like. As for the non-aqueous solvents and suspensions, propylene glycol, polyethylene glycol, vegetable oils such as olive oil, injectable esters such as ethyl oleate, and the like may be used. As a base material of the suppository, witepsol, macrogol, tween 61, cacao butter, laurin paper, glycerogeratin and the like may be used.

According to an embodiment of the present disclosure, the pharmaceutical composition may be administered to the subject in a conventional manner through intravenous, intraarterial, intraperitoneal, intramuscular, intraarterial, intraperitoneal, intrasternal, transdermal, intranasal, inhalational, topical, rectal, oral, intraocular or intradermal routes.

The dosage of the active ingredient according to the present disclosure may vary depending on the condition and weight of the subject, the type and severity of the disease, the type of drug, the route and duration of administration, and may be appropriately selected by those skilled in the art, and the daily dosage may be 0.01 mg/kg to 200 mg/kg, preferably 0.1 mg/kg to 200 mg/kg, and more preferably 0.1 mg/kg to 100 mg/kg. Administration may be administered once a day or divided into several times, and the scope of the present disclosure is not limited thereby.

In addition, the present disclosure provides a health functional food composition for improving or preventing inflammatory diseases including NMN as an active ingredient, and the inflammatory diseases may be caused by NAMPT protein knock out.

The health functional food may contain various nutrients, vitamins, minerals (electrolytes), flavors such as synthetic flavors and natural flavors, colorants and enhancers (cheese, chocolate, etc.), pectic acid and a salt thereof, alginic acid and a salt thereof, organic acids, protective colloidal thickeners, pH regulators, stabilizers, preservatives, glycerin, alcohol, carbonating agent used in carbonated beverages and the like.

In addition, it may contain pulp for the preparation of natural fruit juices, synthetic fruit juices and vegetable drinks. These components may be used independently or in combination. In addition, the health functional food composition may be in the form of any one of meat, sausage, bread, chocolate, candy, snacks, confectionery, pizza, ramen, chewing gum, ice cream, soup, beverage, tea, functional water, drink, alcohol and vitamin complex.

In addition, the health functional food may additionally include food additives, and its suitability as a "food additive" is determined according to the standards and criteria for the item in accordance with the general rules of the Food Additives Code and general test methods approved by the Ministry of Food and Drug Safety unless otherwise specified.

Examples of the items listed in the "Food Additives Code" include chemical synthetic products such as ketones, glycine, potassium citrate, nicotinic acid, and cinnamic acid, natural additives such as persimmon pigment, licorice extract, crystalline cellulose, goreng pigment, guar gum, mixed formulations such as sodium L-glutamate formulation, noodle-added alkali formulation, preservative formulation, tar color formulation, and the like.

At this time, the content of the active ingredient added to the food in the process of manufacturing the health functional food may be appropriately increased or decreased as necessary, and preferably may be added so that 1 part by weight to 90 parts by weight is included in 100 parts by weight of the food.

In addition, the present disclosure provides a reagent composition for increasing NADPH expression including NMN as an active ingredient.

Hereinafter, to help the understanding of the present disclosure, example embodiments will be described in detail. However, the following example embodiments are merely illustrative of the content of the present disclosure, and the scope of the present disclosure is not limited to the following example embodiments. The example embodiments of the present disclosure are provided to more completely explain the present disclosure to those of ordinary skill in the art.

[Example 1] Transcript Profiling in Human Peripheral Blood Mononuclear Cells (PBMCs)

Affymetrix HG-U133A human GeneChip array data; NCBI GEO accession number: GSE3365 was used. Differentially expressed genes (DEG) in human peripheral blood mononuclear cells (hereinafter referred to as PBMCs) of patients with ulcerative colitis (UC; n=26) and Crohn's disease (CD; n=59) as well as normal individuals (NT, n=42) were identified using a permutated student's t-test. Gene ontology analysis was performed using gProfileR of the R package. In addition, the immune cell characteristics of each sample were analyzed using xCell.

[Example 2] NAMPT Knock Out Mouse Model

Nampt$^{f/f}$ mice (C57BL6), which have two loxP sites adjacent to exon 5, were crossed with LyzM-Cre mice (C57BL6) to specifically knock out (KO) NAMPT in myeloid cell lineages including macrophages (Nampt$^{f/f}$LyzMCre$^{+/-}$ mice; hereinafter referred to as KO mice). KO mice (heterozygous) were used as mice knocked out of bone marrow-specific NAMPT, and Nampt$^{f/f}$ mice (wild type; hereinafter referred to as WT mice) were used as controls. The mice were stored at the Ajou University Laboratory Animal Research Center and preserved according to the guidelines of the Institution's Animal Care and Use Committee, which approved all animal procedures (2020-0013).

[Example 3] Colitis Mouse Model and Colitis Evaluation

Age- and gender-matched WT mice and KO mice were administered with 2.5% DSS (MP Biomedicals, Santa Ana, CA, USA) for 7 days and then allowed to recover for 7 days. Colitis severity was determined daily through a scoring system based on the sum of scores for the following parameters: weight loss (0 points=no weight loss/weight gain, 1=5 to 10% weight loss, 2=11 to 15% weight loss, 3=16 to 20% weight loss, and 4=21% or more weight loss); stool consistency (score of 0=normal and well formed, 2=very soft and not formed, and 4=loose stool); and hemorrhagic stool score (0=normal colored stool, 2=red colored stool, 4=bloody stool). The disease activity index (DAI) ranged from 0 to 12.

[Example 4] Colon Lamina Propria Cell Isolation

Extraintestinal adipose tissue and blood vessels were carefully removed from the WT mice and KO mice of Example 2, and the colon was opened longitudinally and washed with cold PBS. The washed colon fragments were digested in collagenase D and 0.1 mg/ml DNase I for 40 minutes. Then, the obtained cell suspension was centrifuged by passing through a 100 μm strainer stacked on a Percoll gradient.

[Example 5] Flow Cytometry

The cell suspension of Example 4 was stained with various combinations of fluorochrome-conjugated antibodies on ice for 20 minutes under dark conditions, wherein the antibodies included anti-CD45 (30-F11), anti-CD1 lb (M1/70), anti-F4/80 (BM8), anti-Ly6G (1A8), anti-Ly6C (HK1.4), anti-MHC II (M5/114.15.2), anti-CD11c (N418), anti-CD206 (MMR) and anti-CD86 (GL-1) (all purchased from Biolegend, San Diego, CA, USA). Samples were obtained from the FACS Canto II Flow Cytometer (BD, Franklin Lakes, NJ, USA). Data were analyzed using FlowJo™ Software (BD).

[Example 6] Histopathology and Immunohistochemistry

Histology was scored blindly using a semi-quantitative scoring system based on the sum of scores for the following parameters: presence of ulceration: 0=none, 1=present but very slight, 2=minimal, 3=moderate, 4=widespread; presence of inflammation: 0=none, 1=minimal, 2=mild, 3=moderate, 4=severe; degree of inflammation: 0=none, 1=mucosal, 2=mucosal+submucosal, 3=mucosal+submucosal+muscle penetration, 4=full thickness invasion. Immunohistochemistry was performed using rabbit anti-NAMPT (Bethyl Laboratories, TX, USA), rabbit anti-Ki-67 (Abcam, Cambridge, UK), rabbit anti-cleaved caspase 3 (Cell Signaling Technology), mouse anti-CD326 (EpCAM)-APC (Invitrogen) and mouse anti-F4/80 (Abcam) antibodies.

[Example 7] Staining for Apoptotic and Phagocytic Cells

Apoptosis was assessed by the TUNEL assay using the Apoptag plus in situ apoptosis fluorescein detection kit (Merck) according to the manufacturer's instructions. TUNEL positive signals were corrected to total nuclear signals for each field. The phagocytic cells were stained using the Apoptag ISOL dual fluorescence apoptosis detection kit (Millipore) according to the manufacturer's instructions. The stained samples were then incubated overnight with mouse anti-F4/80 antibodies. Fluorescence images were obtained by a confocal microscope (A1R HD25, Nikon, Tokyo, Japan) and a slide scanner (Axioscan, Zeiss, Germany).

[Example 8] Evaluation of Phagocytosis pHrodo™ green-conjugated E. coli Bioparticles™ were diluted in serum medium, incubated for 30 minutes and washed twice with PBS. Cells were incubated for the time indicated in the manufacturer's instructions and analyzed using a FACS Canto II flow cytometer (BD) or fluorescence microscope (DFC3000G; Leica, Wetzlar, Germany).

[Example 9] Measurement of NAD$^+$, NADPH and ATP

Bone marrow derived macrophages (hereinafter referred to as BMDM) were harvested, and according to the manufacturer's instructions, EnzyChrom NAD$^+$/NADHA assay Kit (Bioassay Systems, Hayward, CA, USA), Elite NADPH Assay Kit (eEnzyme, Gaithersburg, MD, USA) and Cell Titer-Glo® Luminescent Cell Viability assay (Promega, Madison, WI, USA) were used for analysis.

[Example 10] Measurement of Reactive Oxygen Species (ROS)

BMDM or peritoneal macrophages were incubated with HBSS containing 5 μM CM-H2DCFDA (Invitrogen, Carlsbad, CA, USA) for 15 min at 37° C. To measure mitochondrial reactive oxygen species levels, cells were incubated with 5 μM MitoSOX (Invitrogen) for 15 minutes. FACS Canto II (BD) was used to monitor fluorescence levels.

[Example 11] Statistical Analysis

Data were analyzed using an unpaired two-tailed Student's t-test in GraphPad Prism 9 software (San Diego, CA) and presented as mean±SEM. Statistical significance was set at $p<0.05$.

Figure 2A:
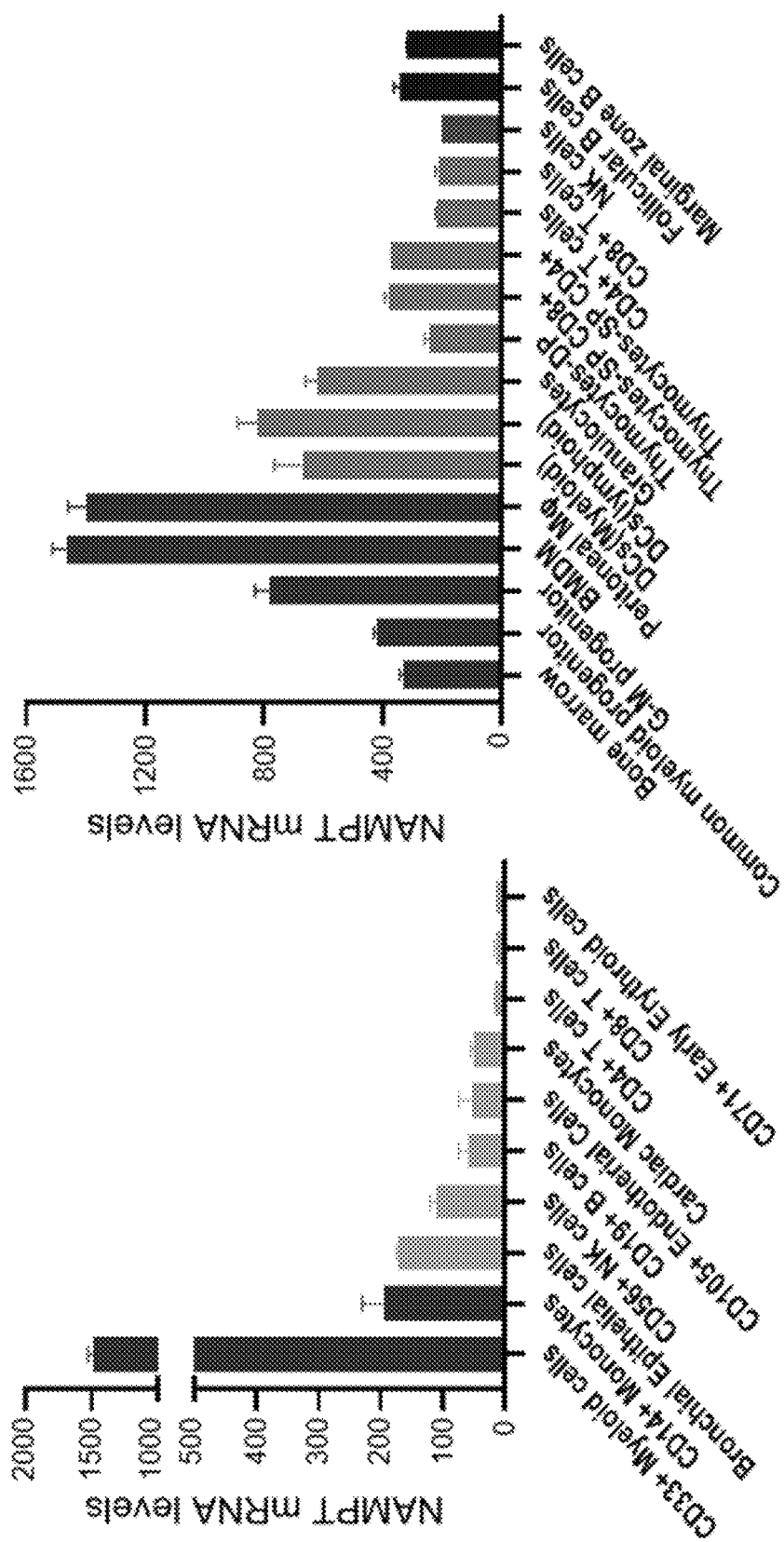
FIGS. 2A to 2D show a test for confirming a correlation with an increase in monocytes and neutrophils in human peripheral blood mononuclear cells (hereinafter referred to as PBMC) of NAMTP-expressing inflammatory bowel diseases (hereinafter referred to as IBD) patients.

[Experimental Example 1] Confirmation of Increased Expression of NAMPT in Inflamed Part NAMPT expression was analyzed in various human tissue samples (data retrieved from public databases) and found that whole blood cells exhibited the highest level of NAMPT expression according to FIG. 1A. The NAMPT expression level in the immune cell subtype was further analyzed and it was confirmed that bone marrow cells exhibited relatively higher levels of NAMPT expression in both humans and mice according to FIG. 2A.

Figure 2B:
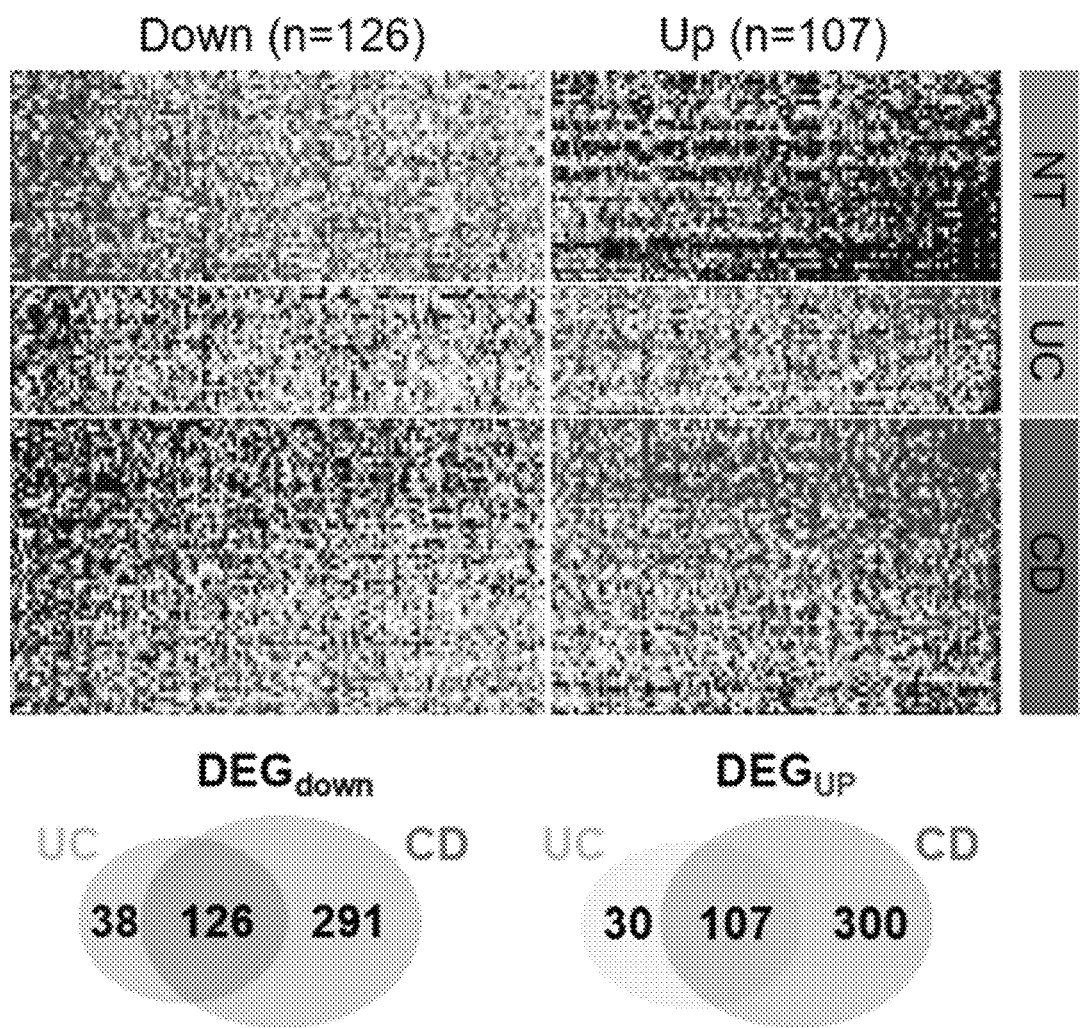

In order to understand the relevance of NAMPT expression patterns in inflammatory disorders, transcriptome data (GSE3365) was analyzed in PBMCs from ulcerative colitis (hereinafter referred to as UC) and Crohn's disease (hereinafter referred to as CD) patients, as well as normal controls (hereinafter referred to as NT) and compared with NT, and according to FIG. 2B, genes commonly up-regulated (n=107) and down-regulated (n=126) were identified in both UC and CD.

Figure 1B:
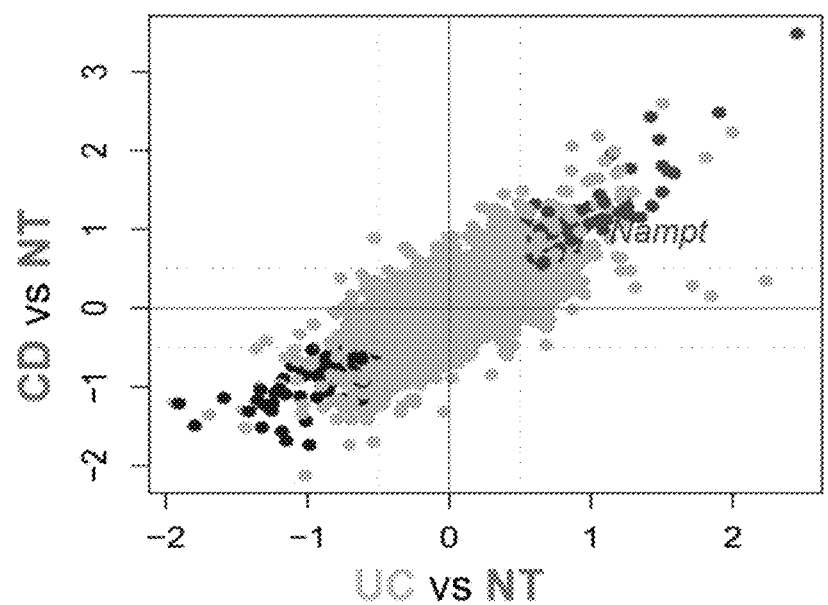
Figure 1C:
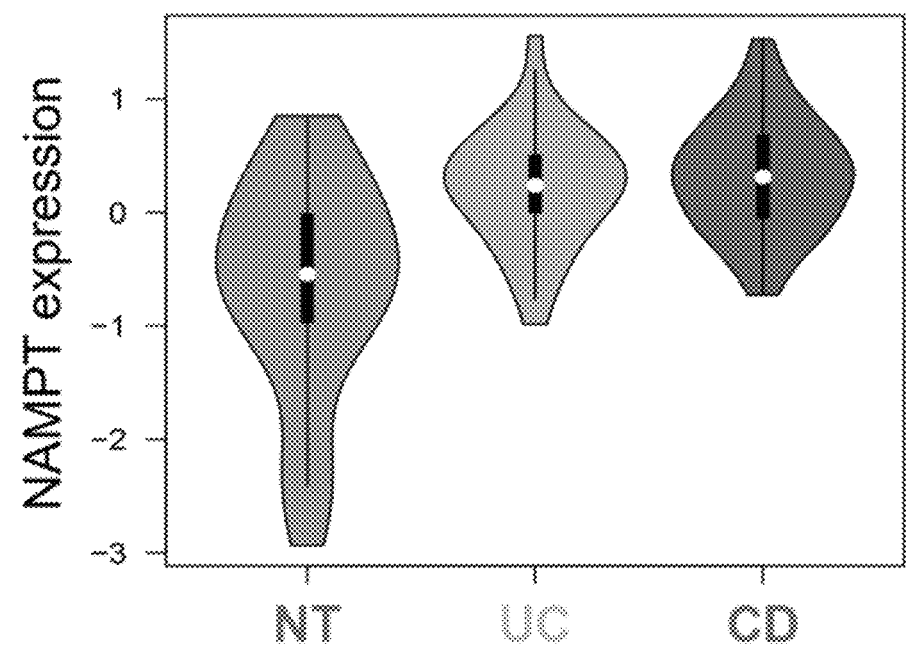
Figure 2C:
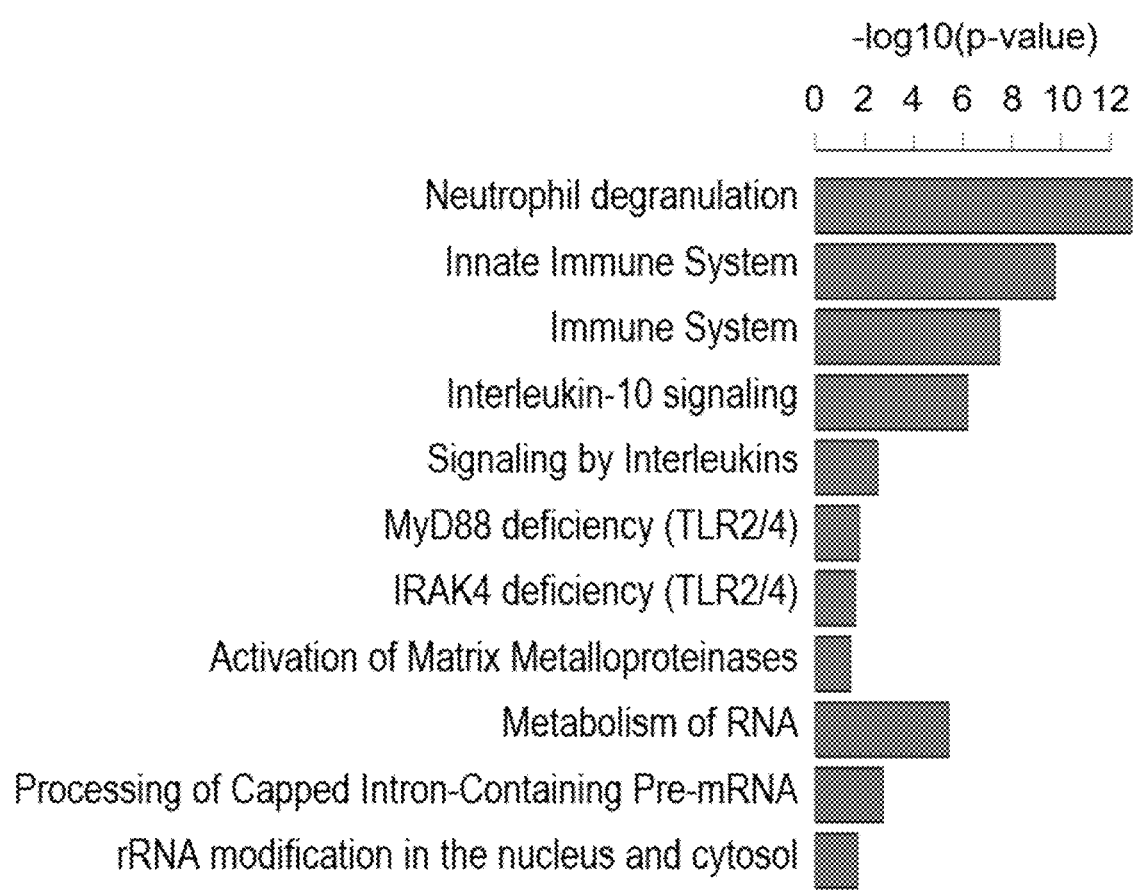

Gene ontology analysis also showed that these up-regulated genes were highly related to leukocyte-mediated immunity according to FIG. 2C, and according to FIG. 1B and FIG. 1C, as expected, it was confirmed that NAMPT was among the up-regulated genes, which could be interpreted as suggesting a pathological role in inflammation.

Figure 2D:
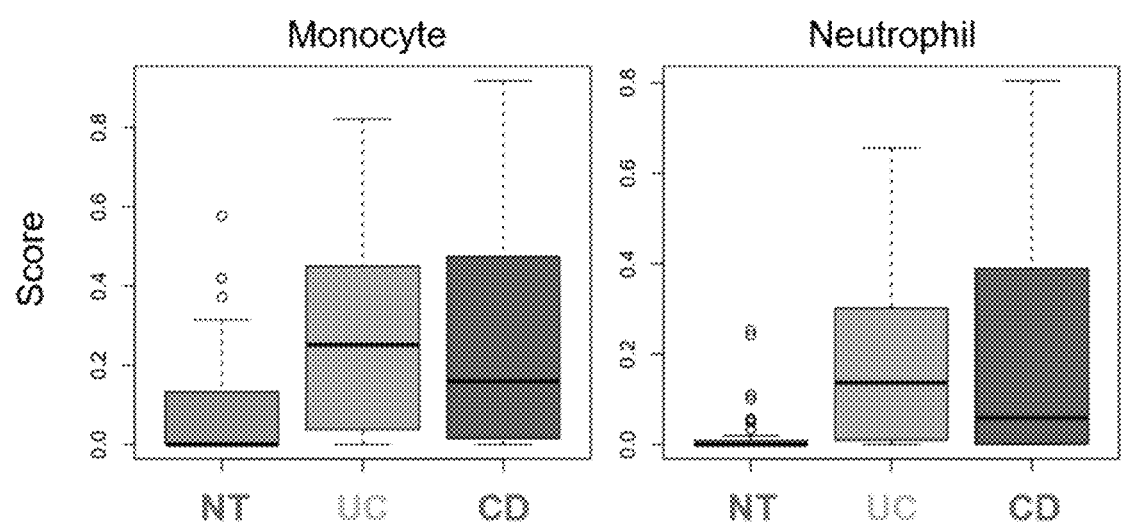

Immune profiling based on transcriptome data showed that myeloid cells were increased in PBMCs of IBD patients according to FIG. 2D, and it could be known that the up-regulated expression of NAMPT in PBMC of IBD patients showed that the increased population of myeloid cells and corresponding cells played an important role in disease progression.

Figure 1D:
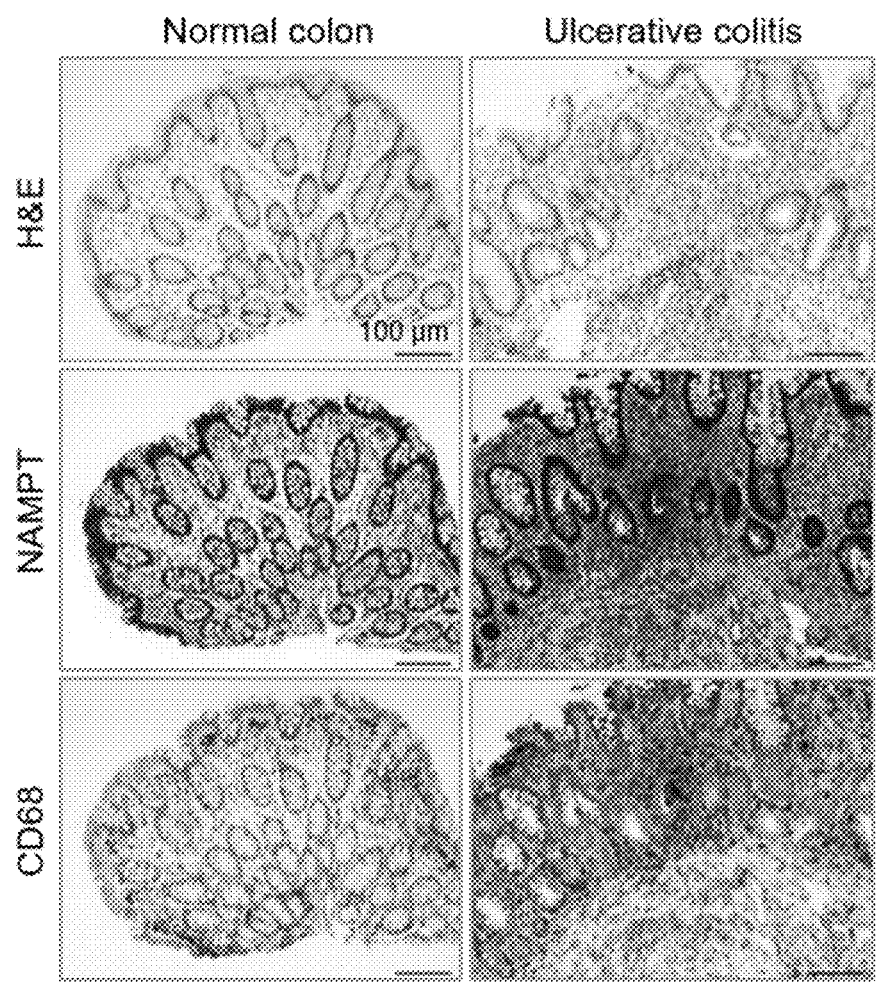

NAMPT expression was analyzed in colon biopsies of IBD patients, and according to FIG. 1D, mucosal biopsies of UC patients showed higher inflammatory cell counts, including CD68 positive macrophages, increased tissue fibrosis, and strong NAMPT expression, in the inflammatory sites than in normal colonic tissue.

Figure 1E:
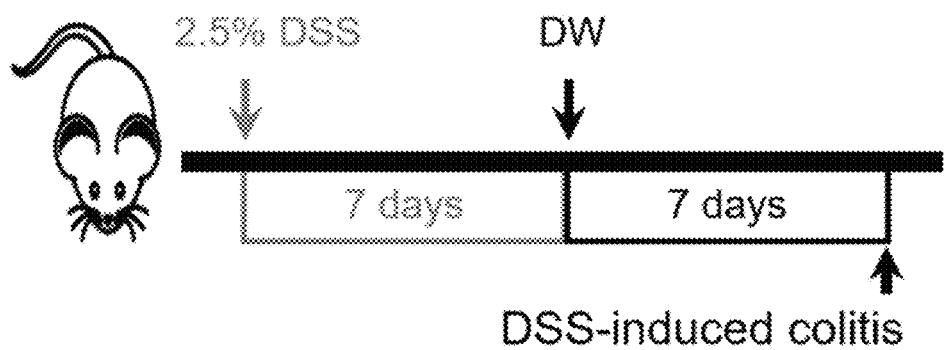
Figure 1F:
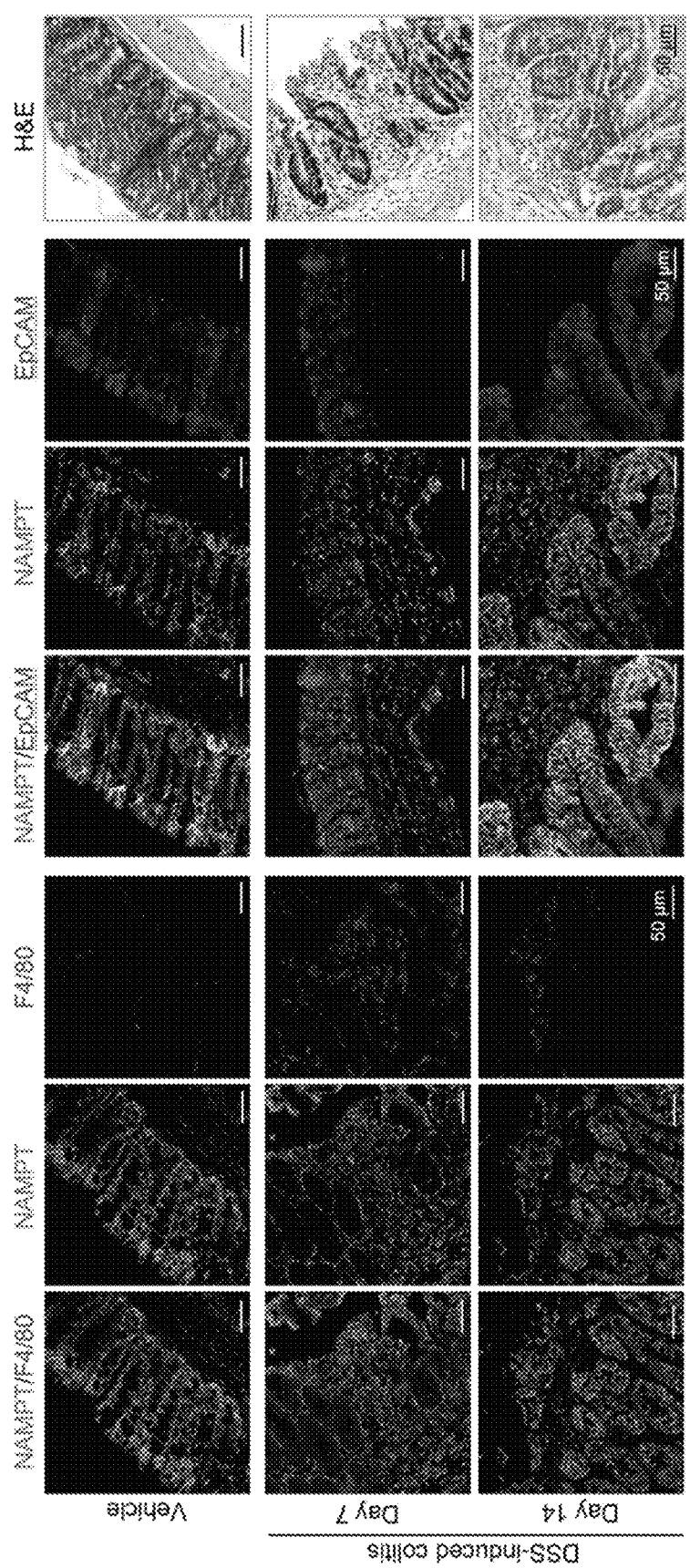

To further understand the pathophysiological role of up-regulated NAMPT in inflammatory diseases, a DSS-induced colitis mouse model (see FIG. 1E) was used, and according to FIG. 1F, disruption of the colonic epithelial structure, increased extent of inflammatory areas, thickened mucosa and a much higher population of day 7 F4/80$^+$ macrophages were found, which were mostly recovered by day 14. Under normal conditions, NAMPT was mainly expressed in the epithelium and co-localized with epithelial cell adhesion molecule (EpCAM), but in DSS-induced colitis, NAMPT expression was detected in both the epithelial and lamina propria, and it was confirmed that NAMPT in the lamina propria colocalized with F4/80 on day 7.

Therefore, it was found that the up-regulated NAMPT expression in inflamed tissues was due not only to transcriptional regulation but also to an increased macrophage population that gathered to the inflammatory site.

Figure 3A:
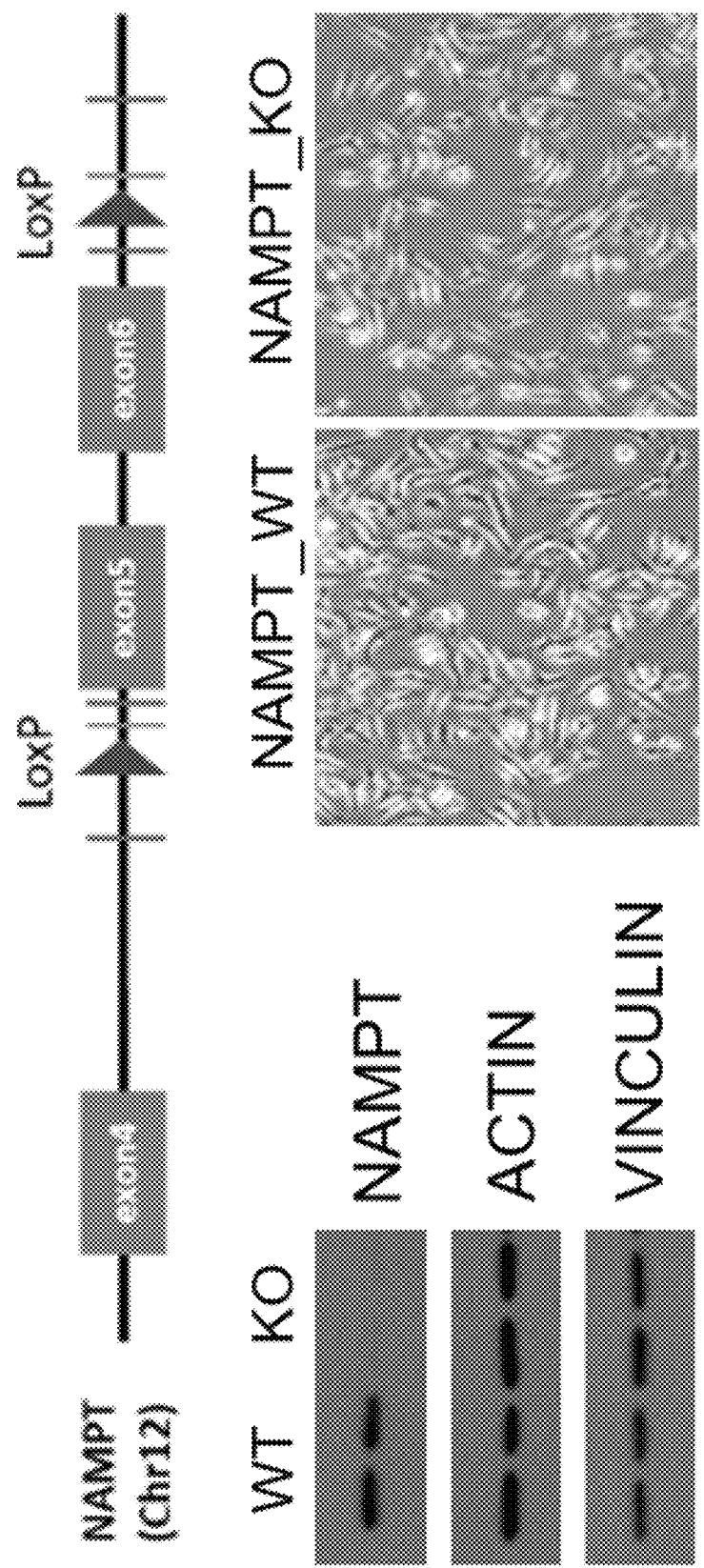
FIGS. 3A to 3H show a test for confirming whether knock out of NAMPT in macrophages increases dextran sulfate sodium (DSS)-induced colitis.
Figure 3B:
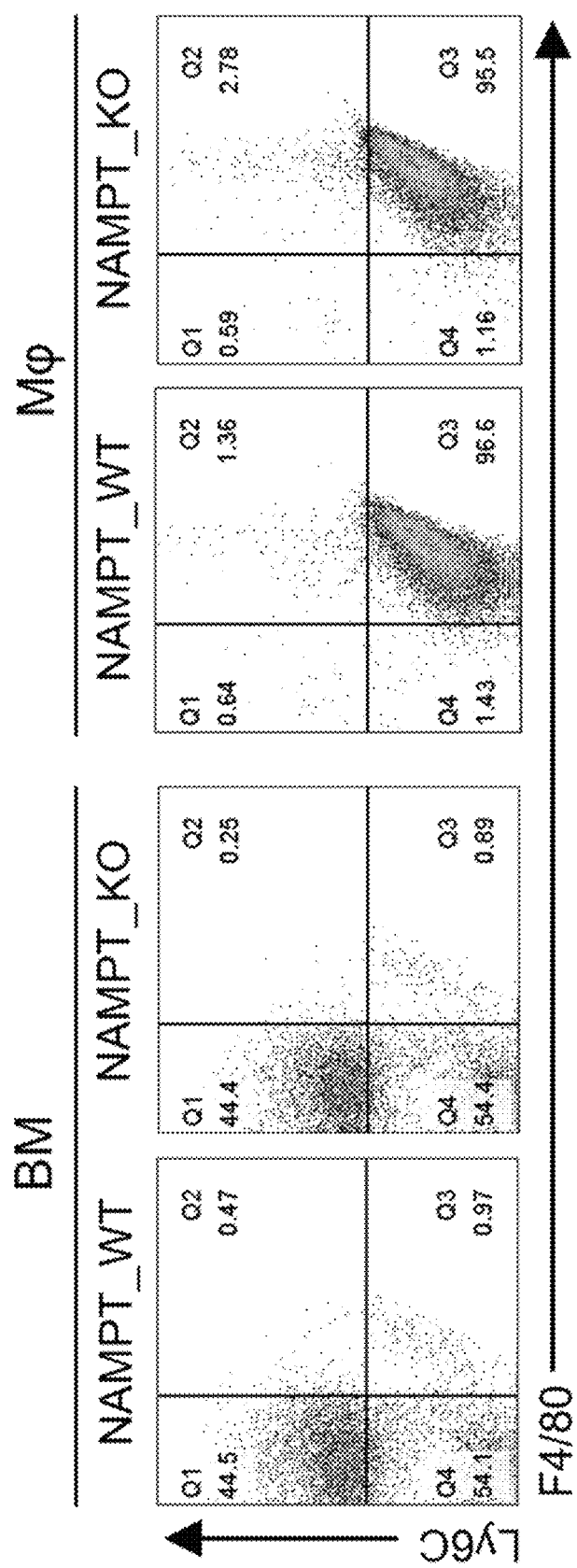
Figure 4:
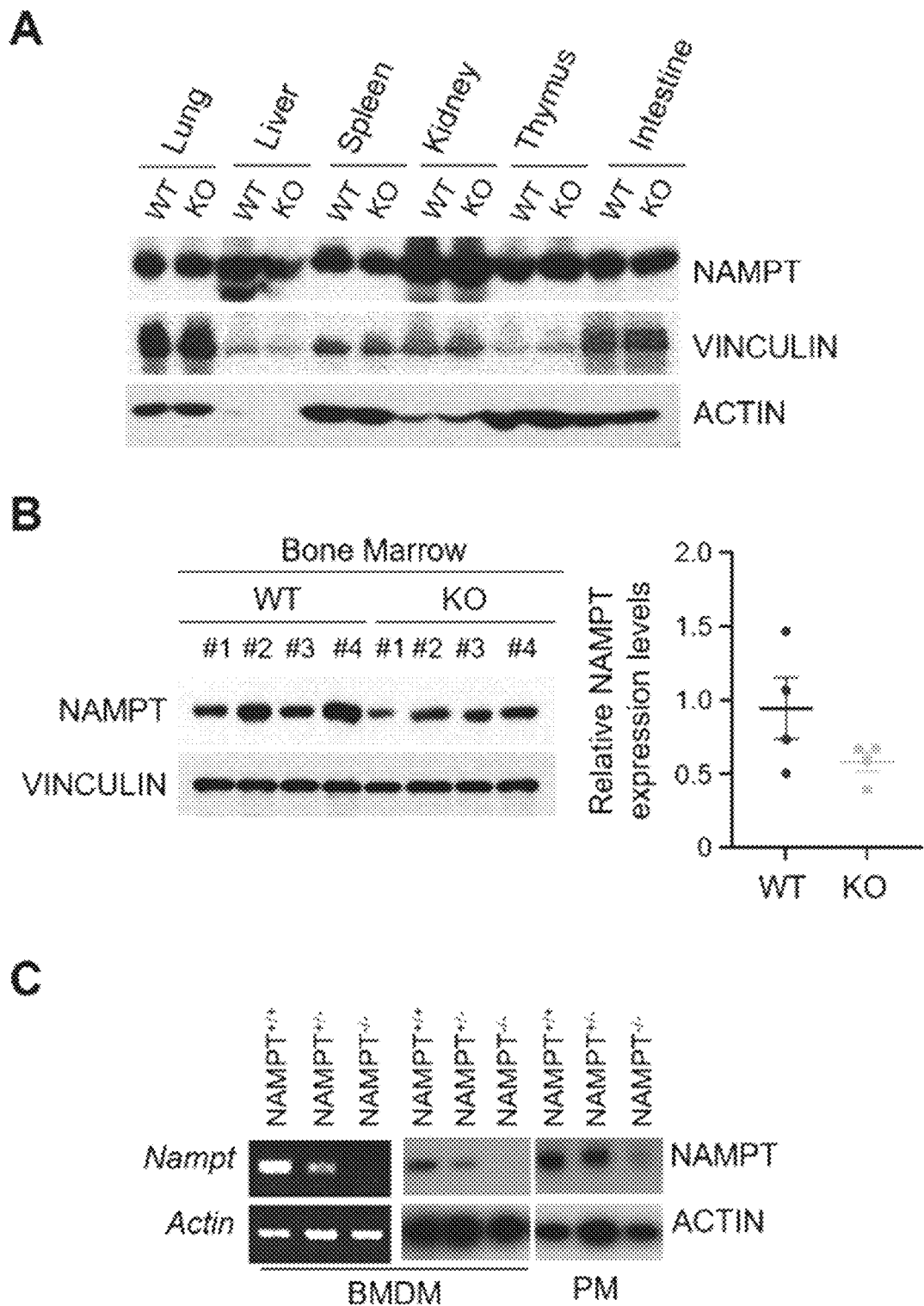
FIG. 4 shows data confirming whether NAMPT is knocked out macrophage-specifically.

[Experimental Example 2] Increase in Severity of Acute Colitis was Confirmed by NAMPT Knock Out in Macrophages In order to investigate the role of myeloid-specific NAMPT in inflammation, according to the top panel of FIG. 3A and Example 2 above, KO mice specifically knocked out of NAMPT in the myeloid compartment (NAMPT$^{f/f}$LysM-Cre$^{+/-}$) was generated. According to FIG. 4A, NAMPT protein expression in other tissues of WT mice and KO mice showed similar patterns, and according to FIG. 4B, the NAMPT protein level of total bone marrow-derived monocytes (hereinafter referred to as BM) of KO mice were reduced by 38% compared to WT mice, whereas it could not be detected in peritoneal macrophages of KO mice, which could be determined that there is a macrophage-specific knock out of NAMPT, according to the lower panel of FIG. 3A and FIG. 4C. For reference, according to FIG. 3B, the ratio of F 4/80$^+$ cells in BMDM was similar between WT mice and KO mice.

Figure 3C:
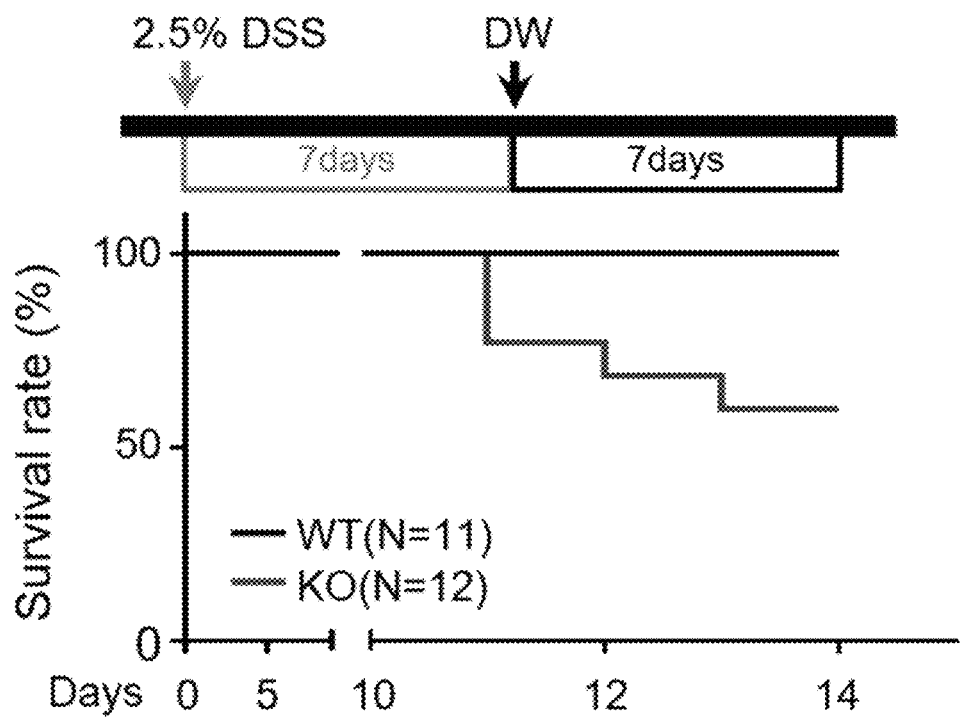
Figure 3D:
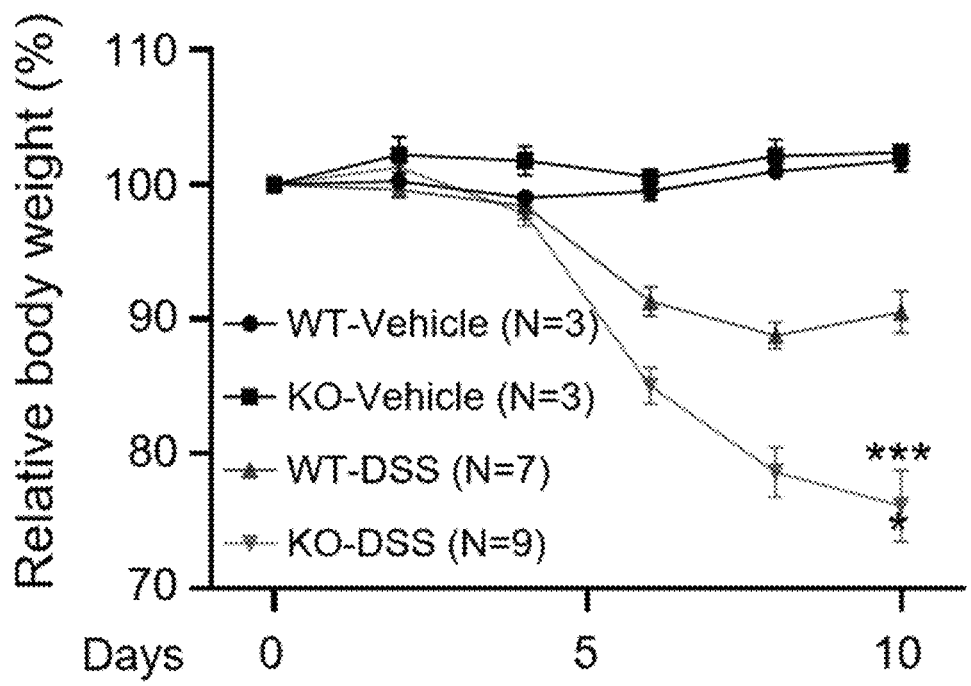
Figure 3E:
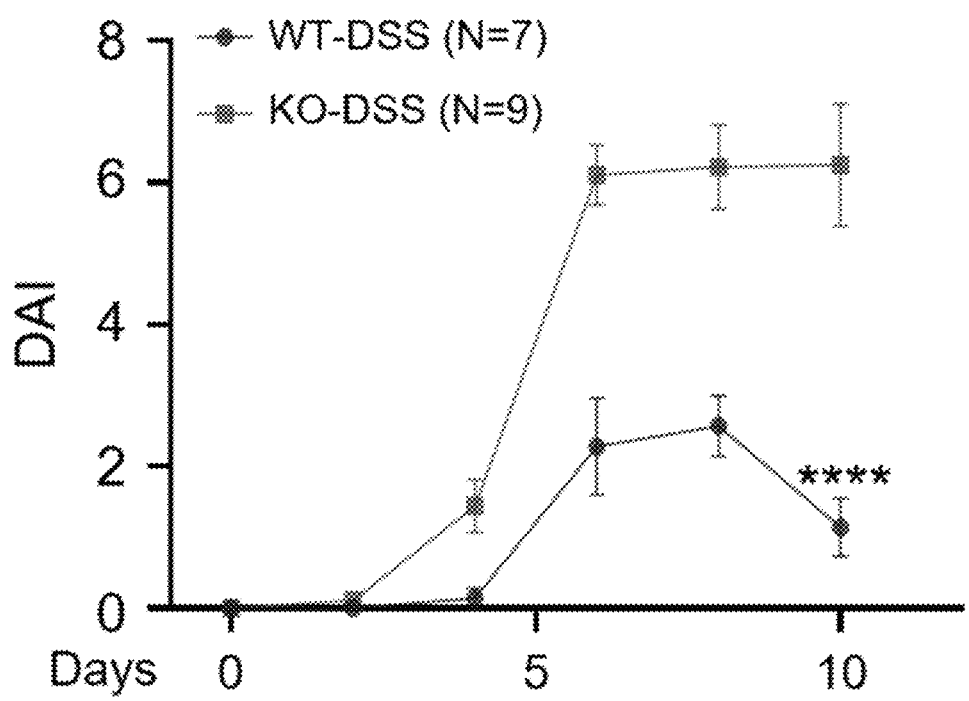

The role of NAMPT in inflammatory macrophages in DSS-induced colitis was investigated. According to FIG. 3C and FIG. 3D, after induction of colitis, all WT mice regained their body weight and survived, even though they lost 10% of their body weight by day 10, but KO mice suffered more severe disease and lost 24% of their body weight, and 42% of KO mice died. In addition, according to FIG. 3E, a dramatic difference in disease activity index (DAI) was observed between WT mice and KO mice, which was interpreted as a protective role of macrophage-derived NAMPT in the context of colitis.

Figure 3F:
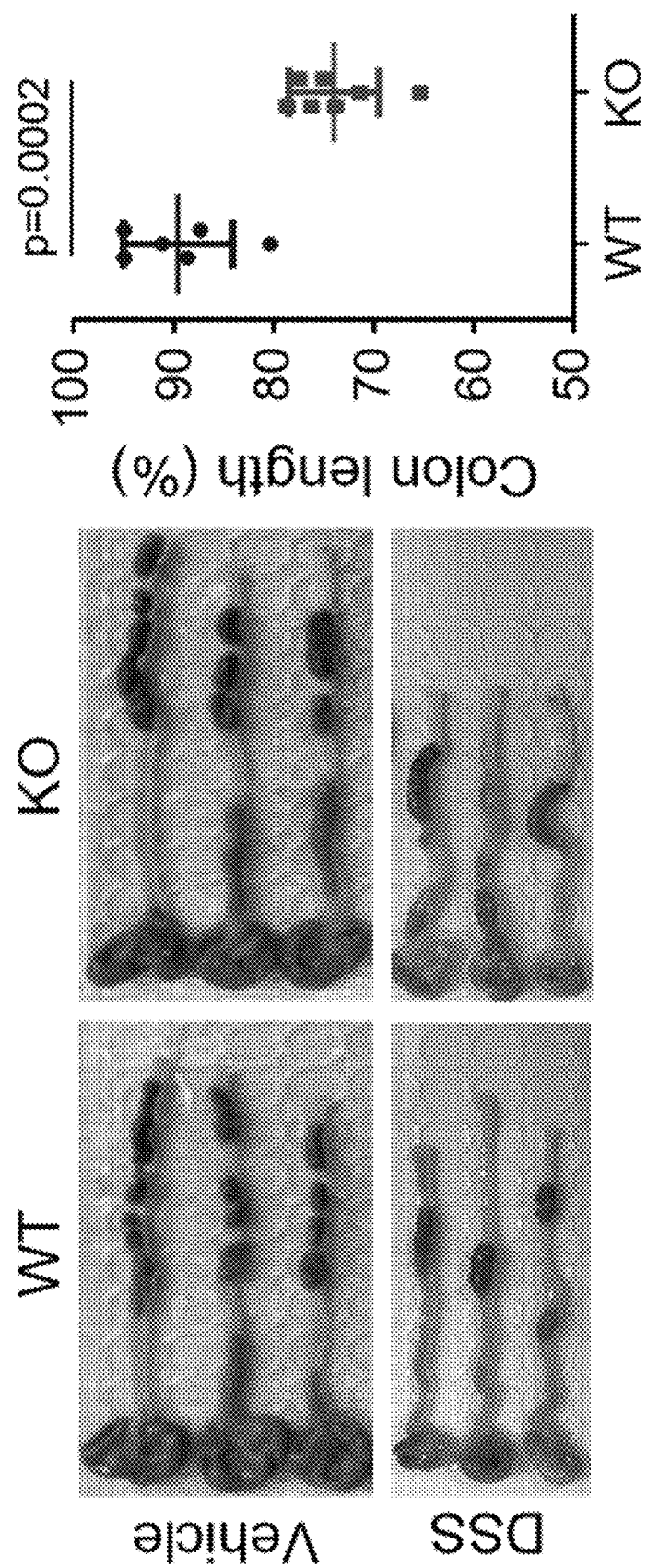
Figure 3G:
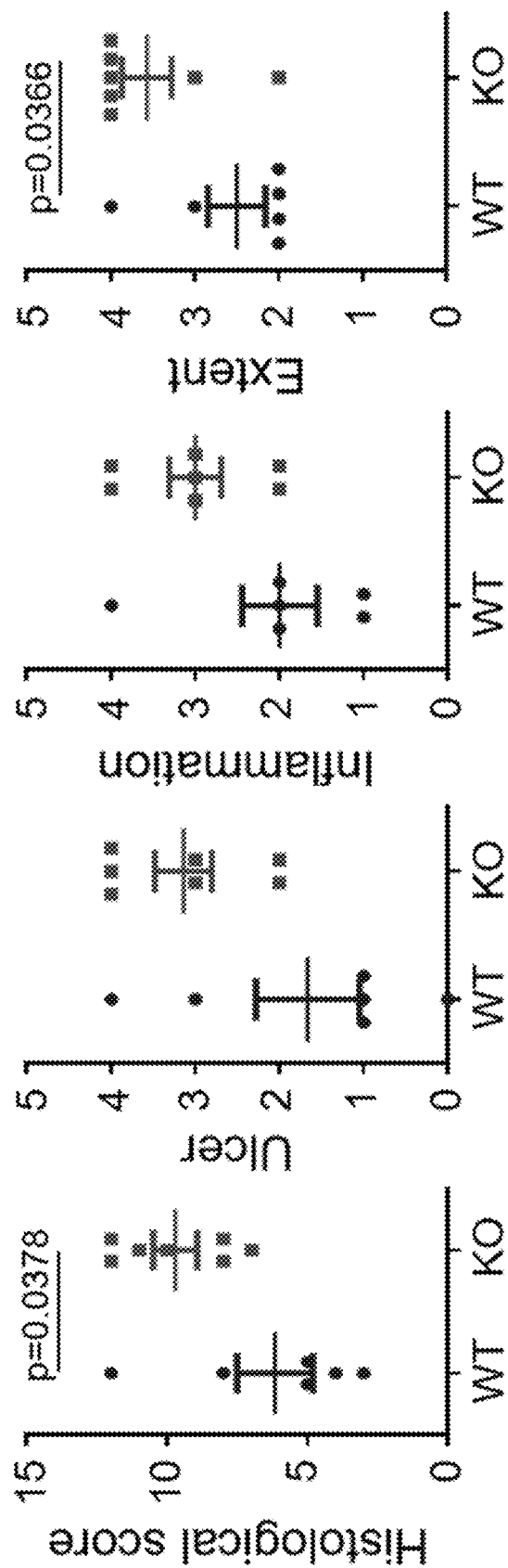
Figure 3H:
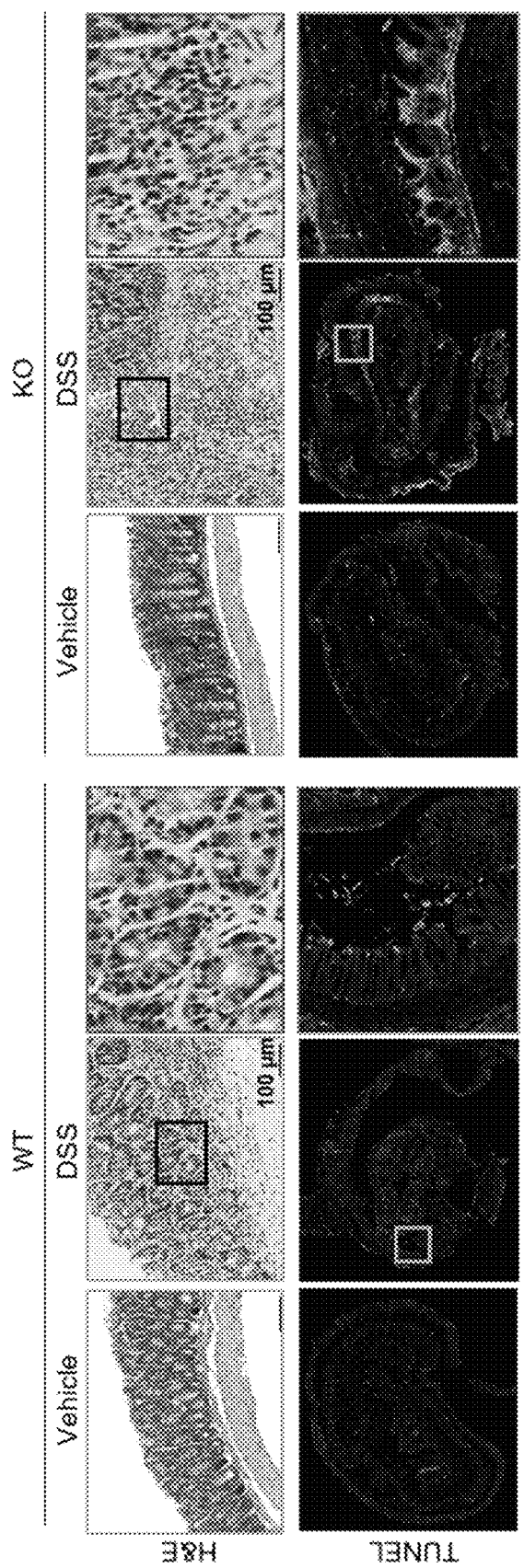

The colon length was checked 14 days after DSS treatment, and according to FIG. 3F, it was significantly shorter in KO mice than in WT mice. Scores by observer blinding were also checked, and according to FIG. 3G, it was confirmed that KO mice showed significantly greater histological scores and tissue destruction as well as the severity of inflammation and ulceration than WT mice upon DSS treatment. In addition, according to FIG. 3H, it was also found that KO mice had more tunel-positive (TUNEL$^+$) cells in colon tissue than WT mice. Therefore, these results confirmed that macrophage-specific NAMPT knock out increases the severity of DSS-induced colitis in a mouse model.

Figure 5A:
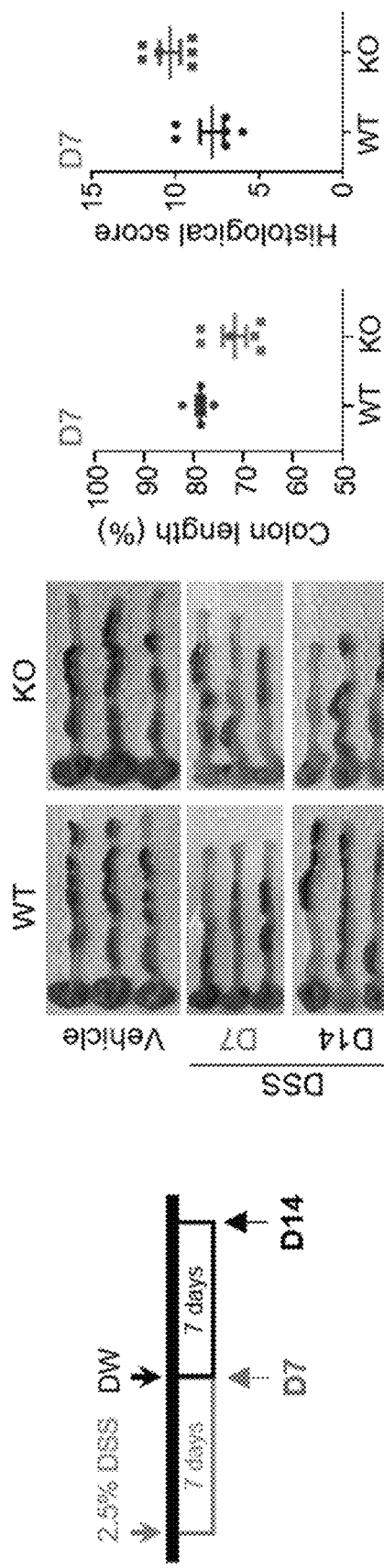
FIGS. 5A to 5H show a test for confirming whether NAMPT-knocked out macrophages change an initiation of an inflammatory response.
Figure 5B:
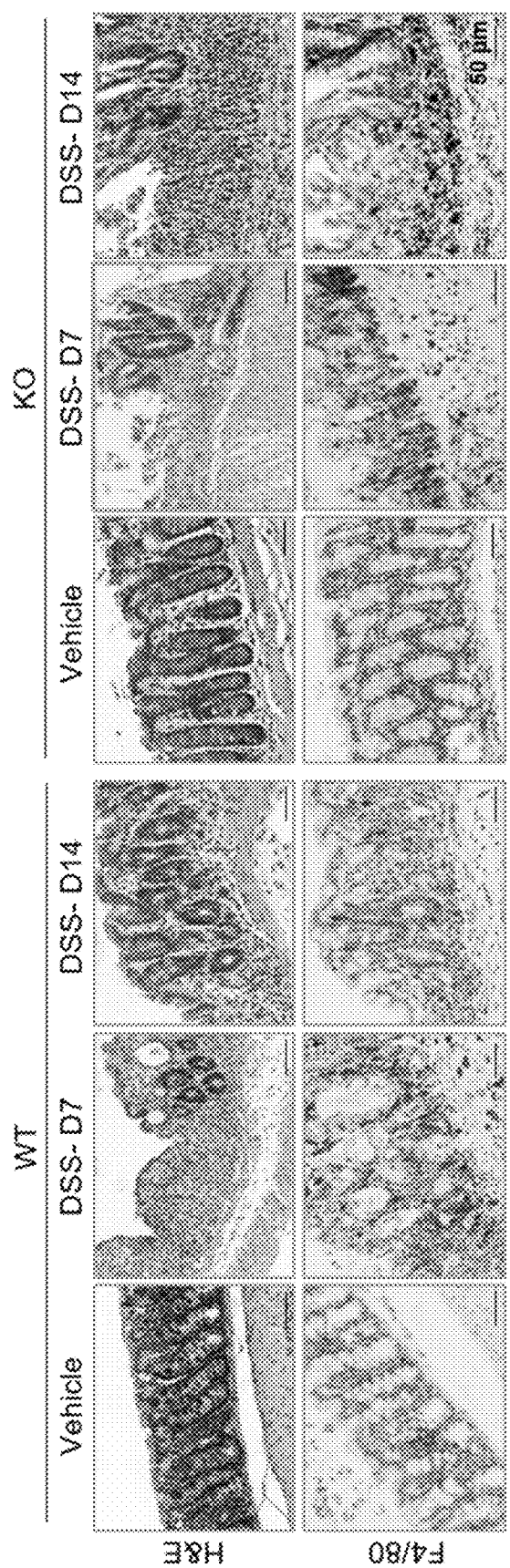
Figure 6A:
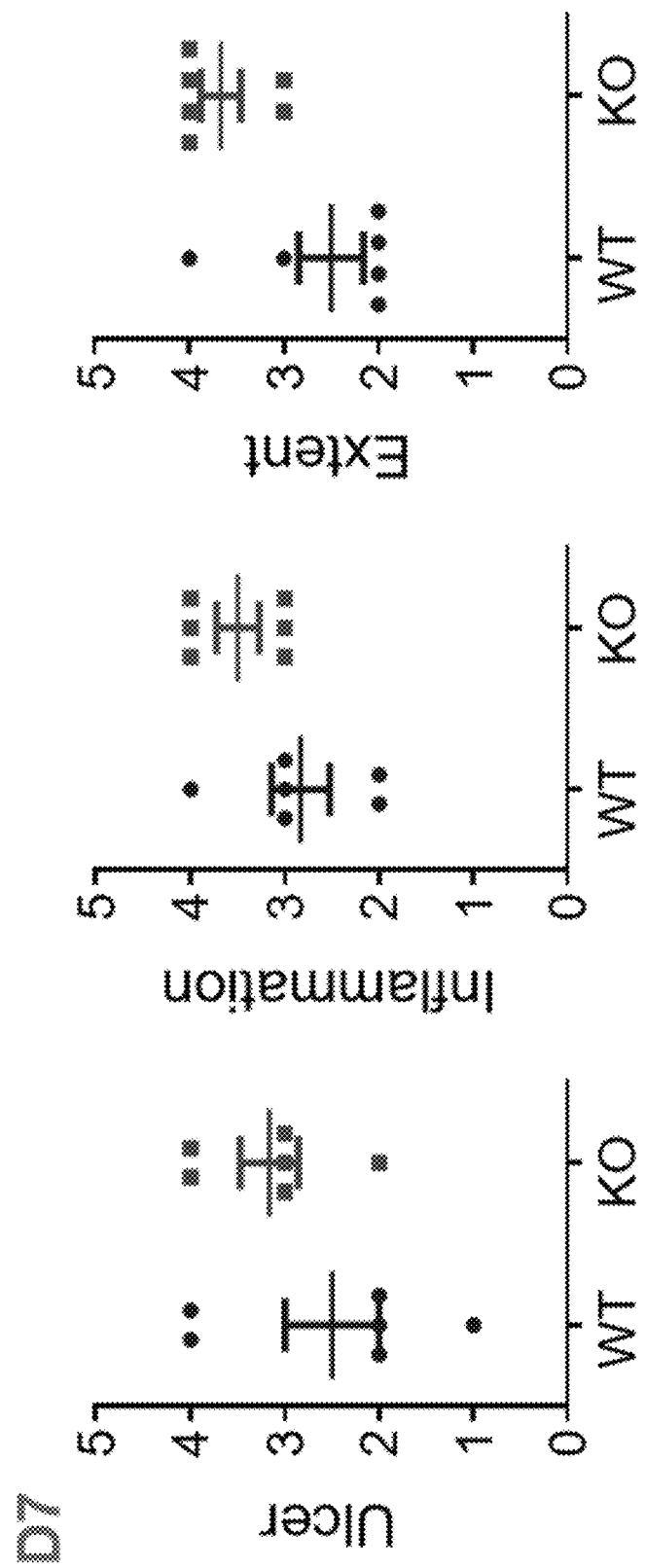
FIGS. 6A to 6D show a test for confirming whether or not myeloid cell mobilization to colon tissue is affected upon DSS treatment when NAMPT is knocked out macrophage-specifically.

[Experimental Example 3] Confirmation of Initiation of Inflammatory Response Due to NAMPT Knock Out In order to identify the degree of contribution of NAMPT to DSS-induced colitis, the degree of recovery was confirmed by comparing the disease state of the mice treated as in Example 3 for the first 7 days and the subsequent 7 days. According to FIG. 5A and FIG. 6A, KO mice showed severe weight loss and colon shrinkage on day 14, and in terms of colon length, KO mice were shorter than WT mice, and histological scores, degree of inflammation, and ulceration were confirmed to be higher in KO mice on day 7. In addition, according to FIG. 5B, the colon tissues of WT mice and KO mice showed severe destruction with a high population of macrophages aggregated on day 7, whereas it was confirmed that, unlike the KO mice, the WT mice normally recovered as evidenced by the length of the colon and the reduced population of macrophages at day 14.

Figure 5C:
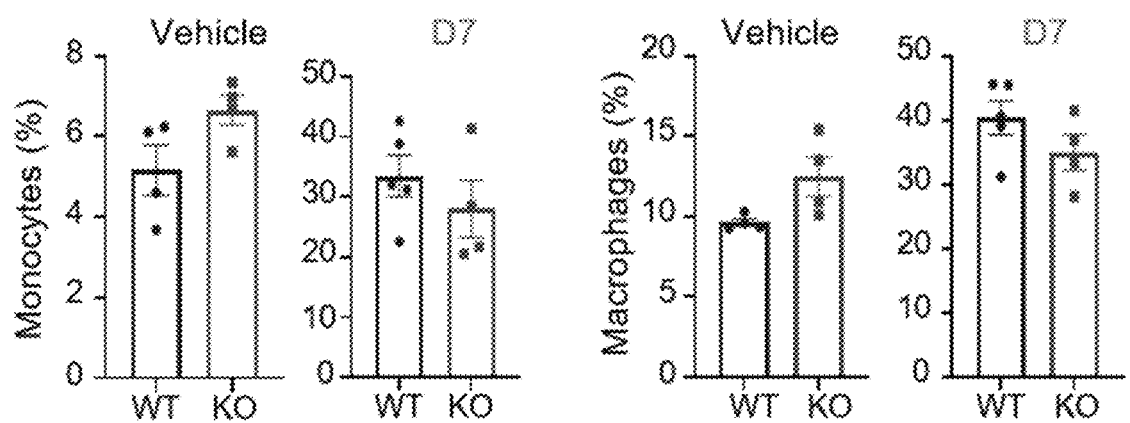
Figure 5D:
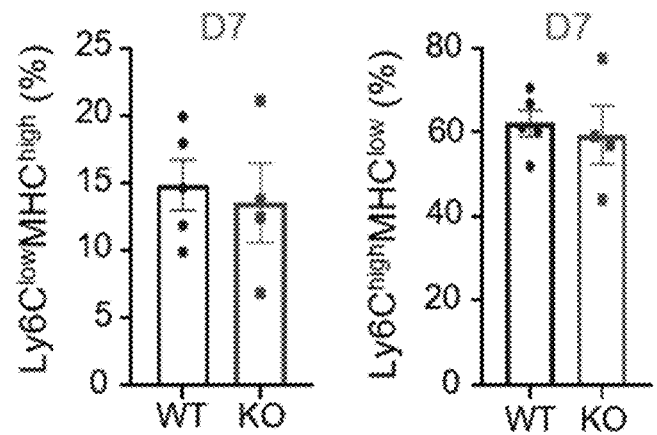
Figure 6B:
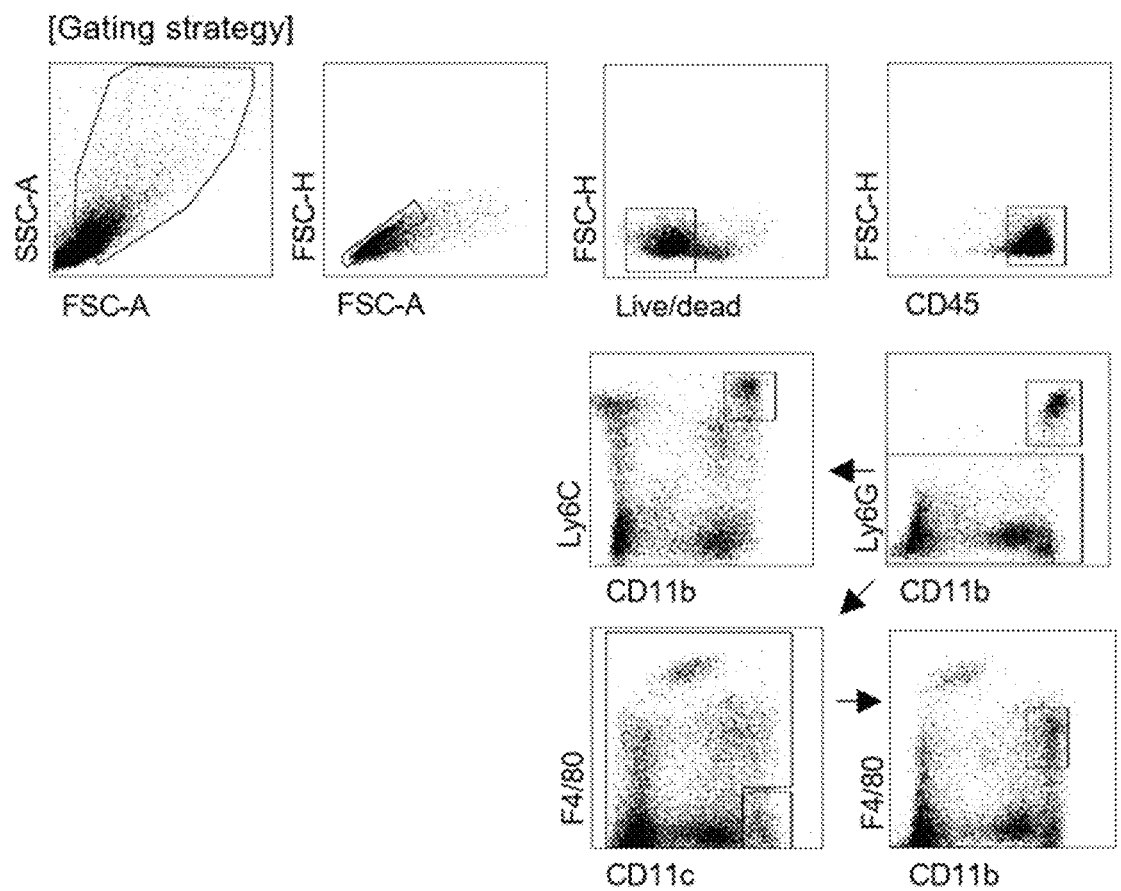
Figure 6C:
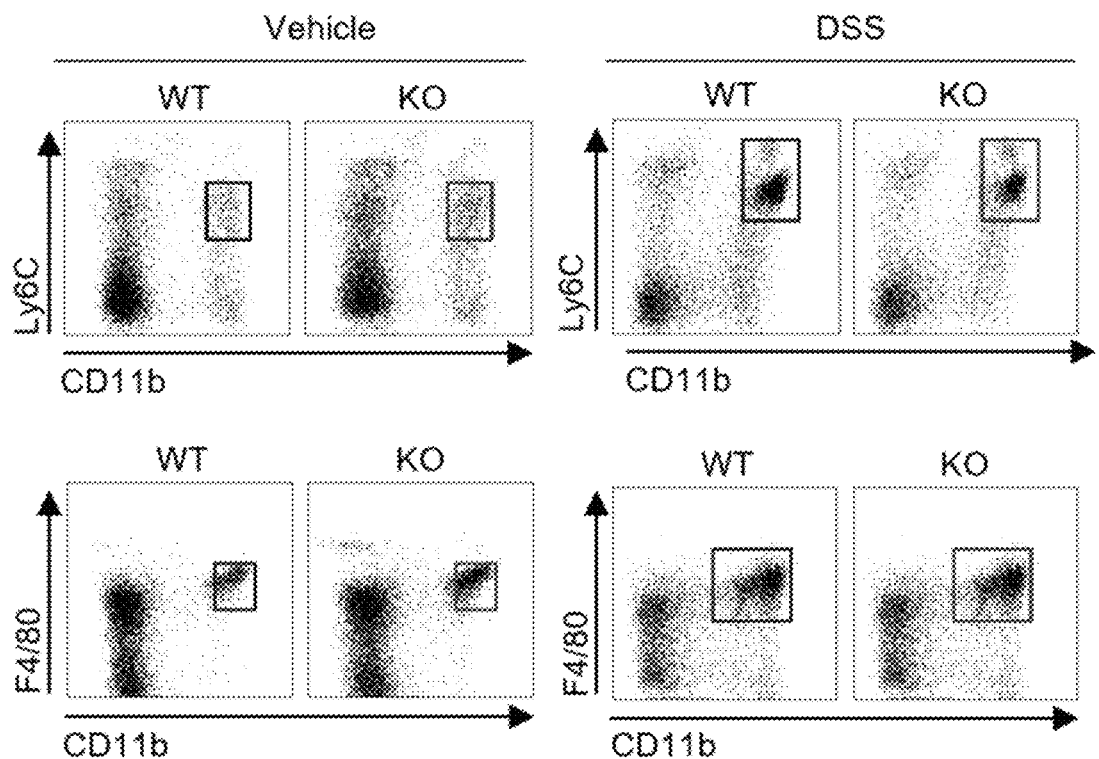
Figure 6D:
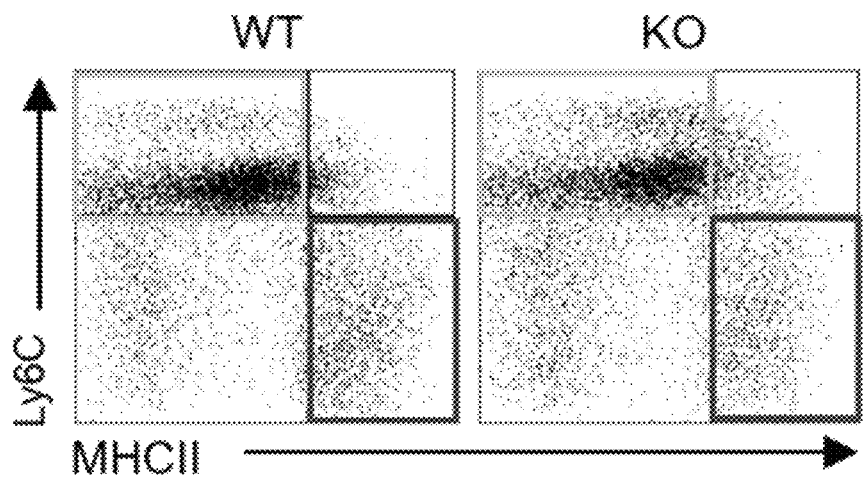

In addition, the ratio of monocytes and macrophages was measured on day 7, and as a result, according to FIG. 5C, FIG. 6B and FIG. 6C, the ratio of monocytes and macrophages was found to be similar between WT mice and KO mice. Additionally, the ratio of pro-inflammatory Ly6C$^{high}$MHC-II$^{low}$ macrophages and Ly6C$^{low}$MHC-II$^{high}$ macrophages was also measured, and as a result, according to FIG. 5D and FIG. 6D, the ratio was similar between WT mice and KO mice, indicating that NAMPT knock out in macrophages did not affect the local aggregation of monocytes and macrophages.

Figure 5E:
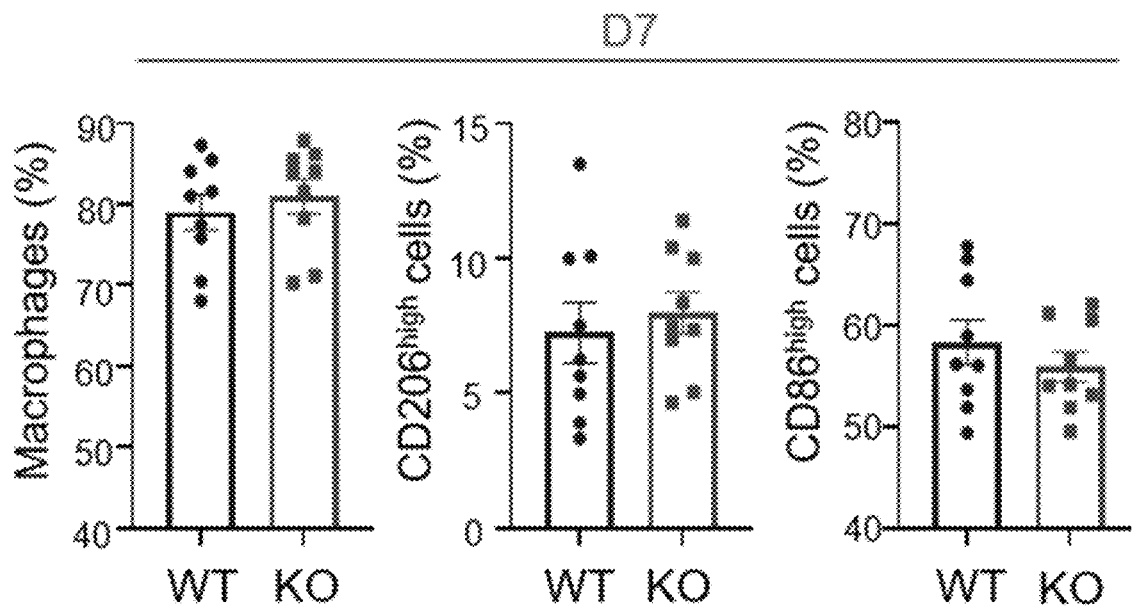
Figure 5F:
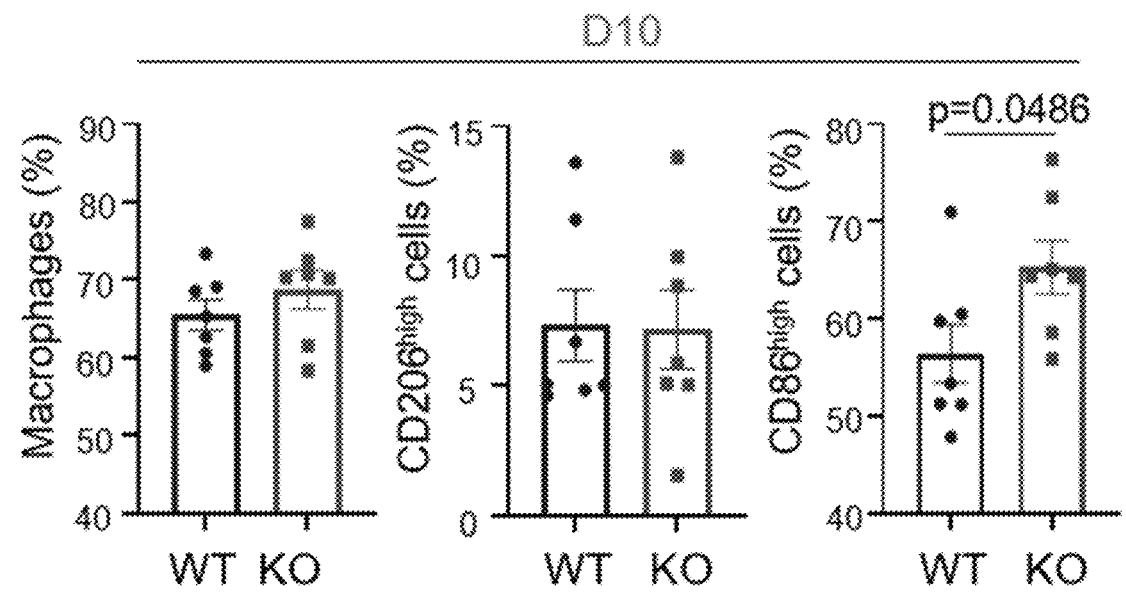
Figure 5G:
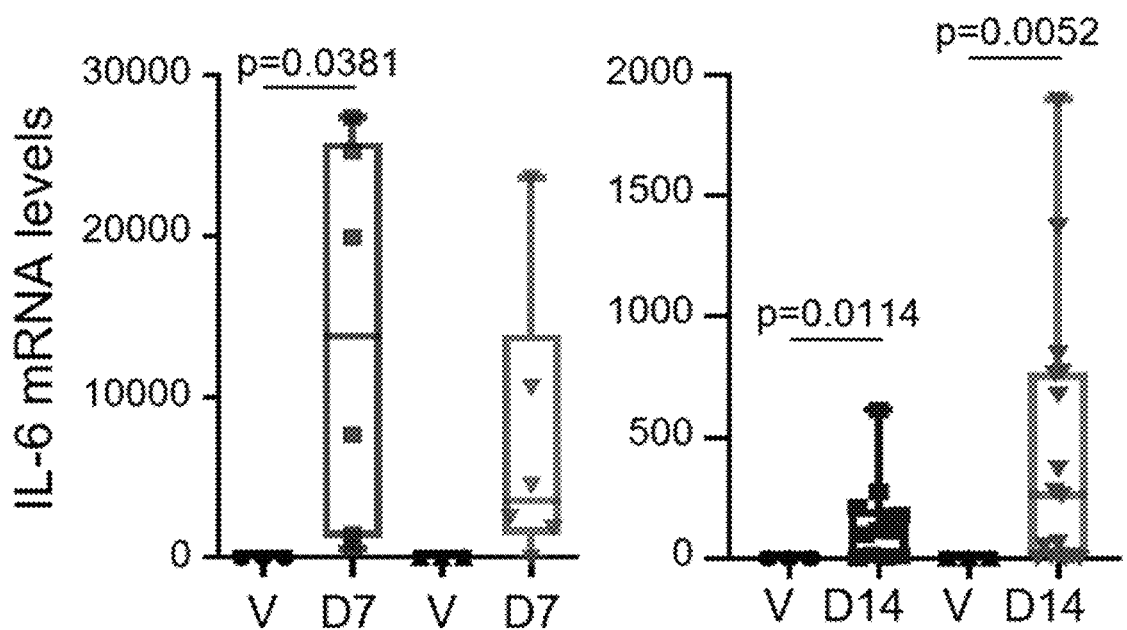
Figure 5H:
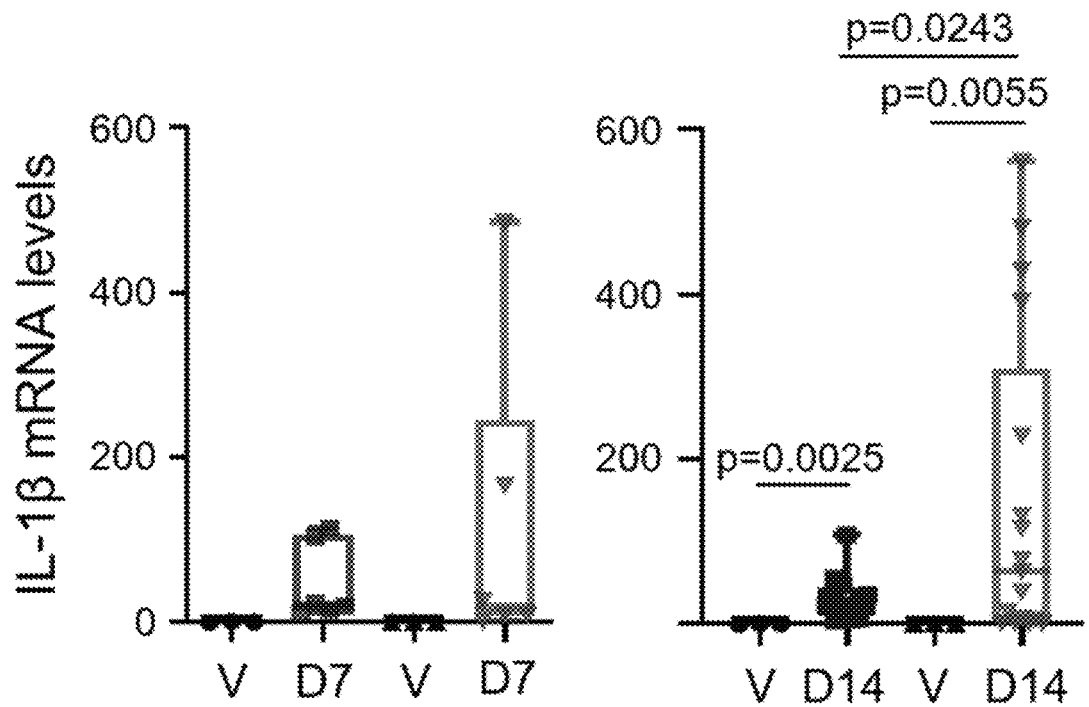

[Experimental Example 4] Relationship Between the Severity of Colitis in NAMPT Knocked Out Mice and the M1/M2 Macrophage Phenotype To determine whether NAMPT knock out changes the M1 and M2 macrophage populations during the development of colitis, the ratio of M1 and M2 macrophages in the colonic mucosa in DSS-induced colitis from the mice of Example 3 was analyzed. As a result, according to FIG. 5E, on day 7, the ratio of F4/80$^+$CD11b$^+$ macrophages and the percentage of M1 (CD86$^{high}$) and M2 (CD206$^{high}$) macrophages were similar between KO mice and WT mice upon DSS treatment, and according to FIG. 5F, the population of M1 (CD86$^{high}$) macrophages was higher in KO mice than in WT mice during convalescence and this was consistent with histological examination. M1 and M2 macrophages are characterized by the secretion of proinflammatory cytokines and antiinflammatory cytokines, respectively, and according to FIG. 5G and FIG. 5H, with a similar pattern of colonic M1 and M2 macrophage populations, we found strong induction of inflammatory genes at day 7 during DSS treatment, but no significant effect of NAMPT knock out, but after the convalescence, the KO mice still had a high macrophage population in the inflamed tissue (see FIG. 5B), and accordingly, it was confirmed that the expression of inflammatory genes was up-regulated in the intestinal samples compared to the WT mice.

Figure 7:
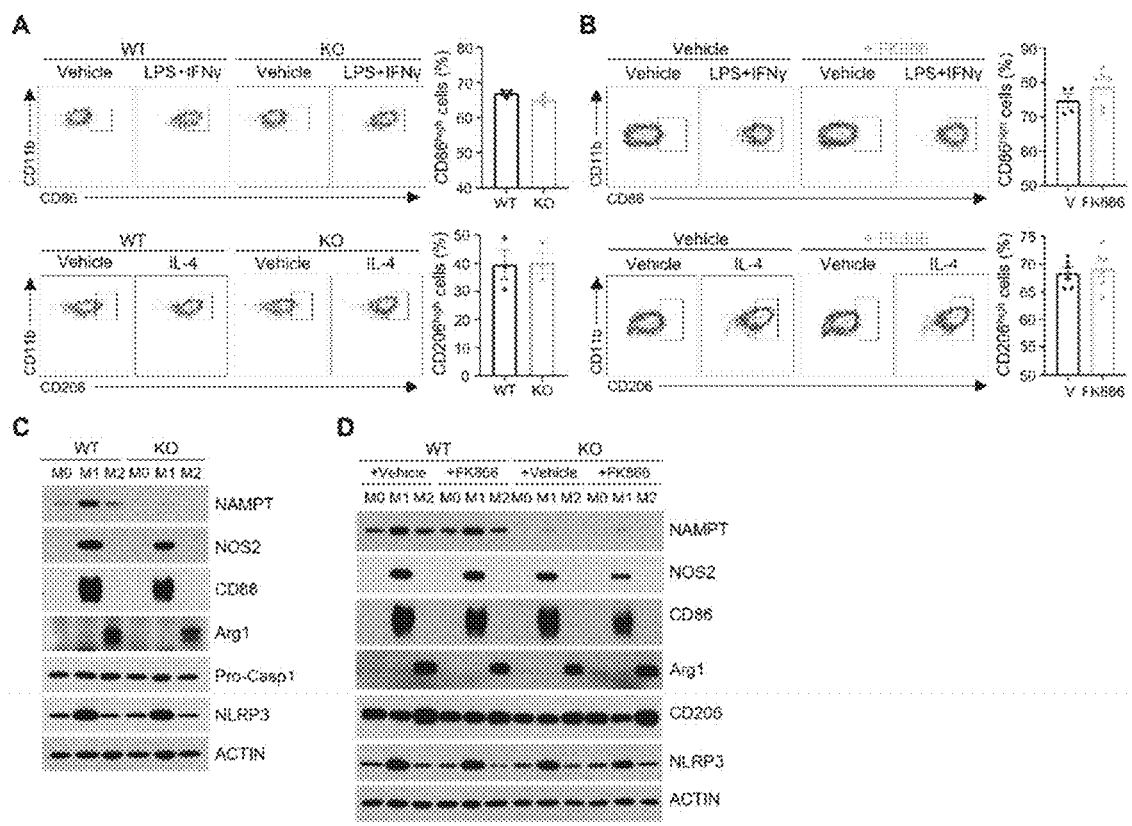
FIG. 7 shows a test for confirming whether NAMPT knock out affects macrophage polarization.

Next, it was determined whether NAMPT is involved in the polarization of M1 and M2 macrophages. BMDM can differentiate into M1-like macrophages when treated with LPS/IFN-γ and into M2-like macrophages when treated with IL-4, and according to FIG. 7A and FIG. 7B, NAMPT knock out did not result in polarization of M1 and M2 macrophages, nor did inhibition of NAMPT enzymatic activity by FK866 treatment. Expression levels of specific markers representing various states of macrophages were further analyzed by Western blot, and as a result, according to FIG. 7C, there was no significant difference between macrophages between WT mice and KO mice, and it was found that NAMPT expression did not inhibit polarization of M1 and M2 macrophages during the inflammatory process. Similar to FACS analysis, according to FIG. 7D, FK866 treatment did not affect the expression of M1 and M2 macrophage-specific markers.

Figure 8A:
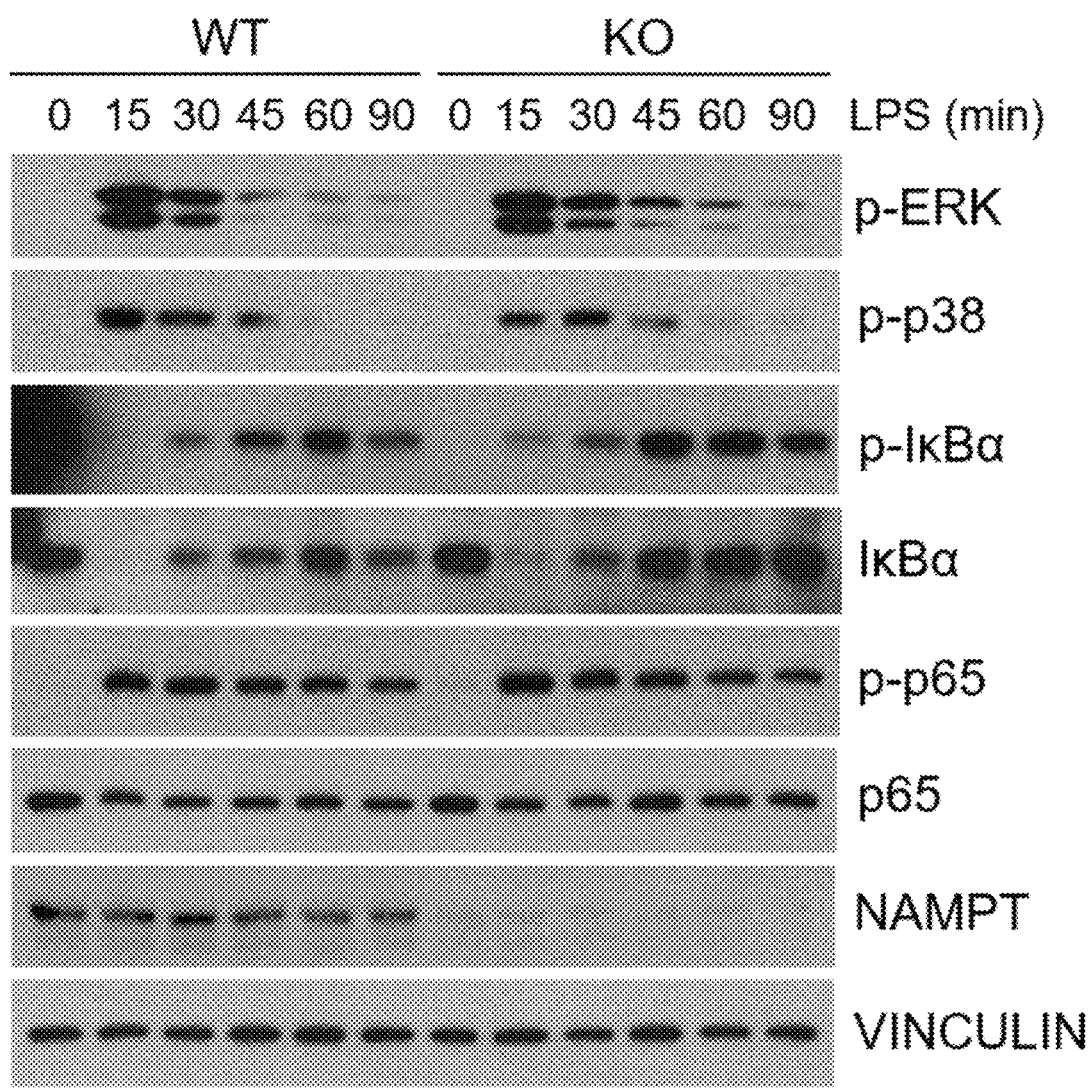
FIGS. 8A to 8E show a test for confirming whether NAMPT knock out alters TLR4 downstream signaling.
Figure 8B:
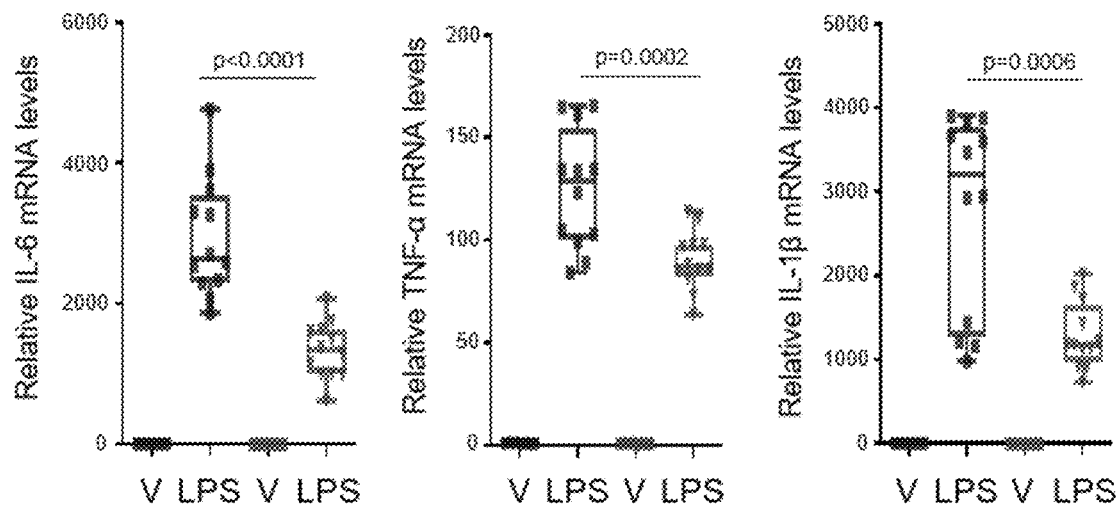
Figure 8C:
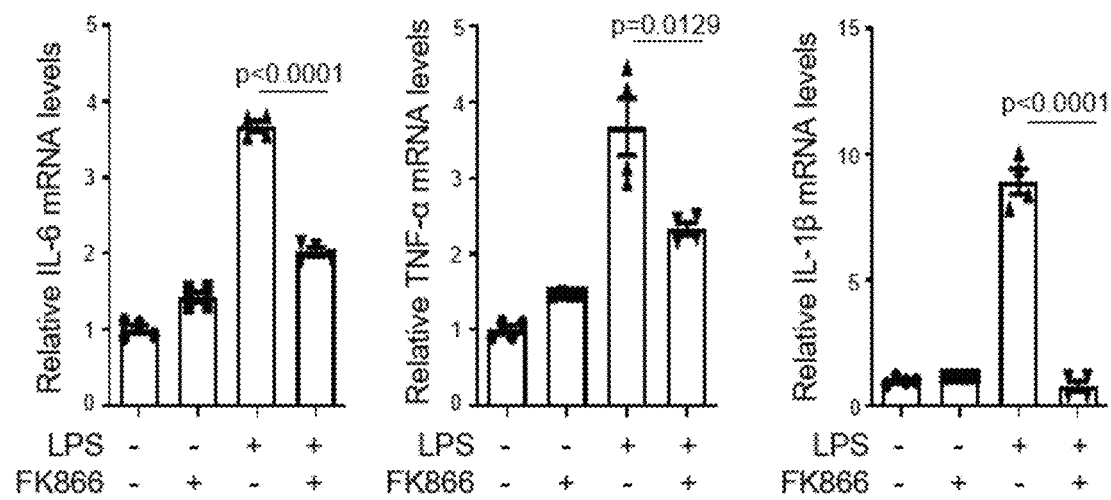
Figure 8D:
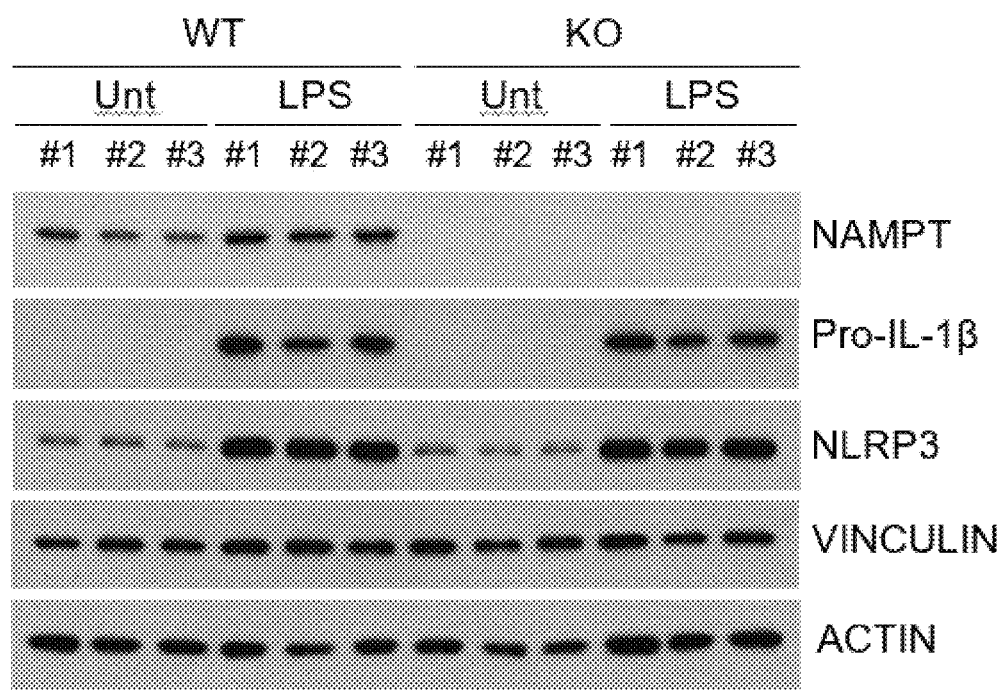
Figure 8E:
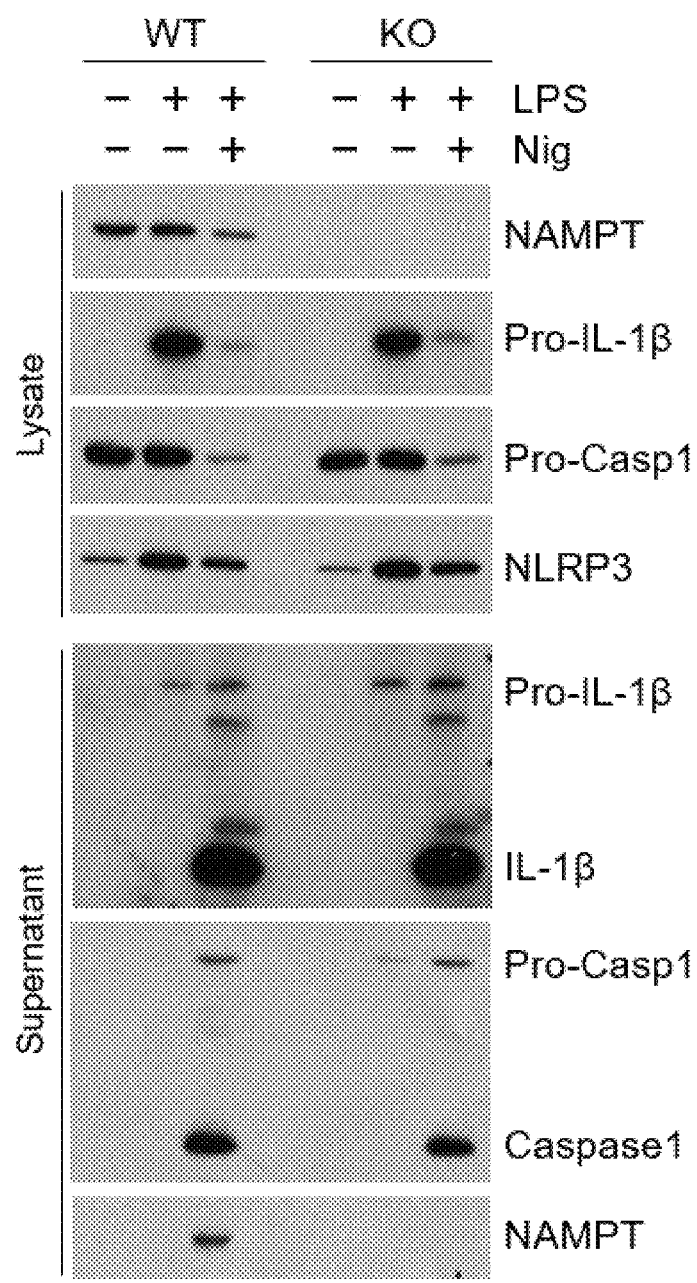

Changes in TLR4 late signal transduction were confirmed, and as a result, according to FIG. 8A, BMDM of WT mice and KO mice showed no change in TLR4 late signal transduction such as MAPK and NF-κB activation in response to LPS. On the other hand, according to FIG. 8B to FIG. 8D, in the case of NAMPT knock out, LPS treatment could reduce the mRNA level of cytokines, but at the protein level, IL-1β production in both BMDMs from WT and KO mice showed a similar pattern upon LPS treatment for 5 hours. In addition, according to FIG. 8E, activation of inflammasome, which is an innate immune system responsible for activation of inflammatory responses, was also confirmed to be similar between BMDMs of WT mice and KO mice.

Taken together, it was found that NAMPT knock out can affect the subsequent steps leading to resolution of inflammation without increasing the severity of DSS-induced colitis by inhibiting macrophage polarization and cytokine production.

Figure 9A:
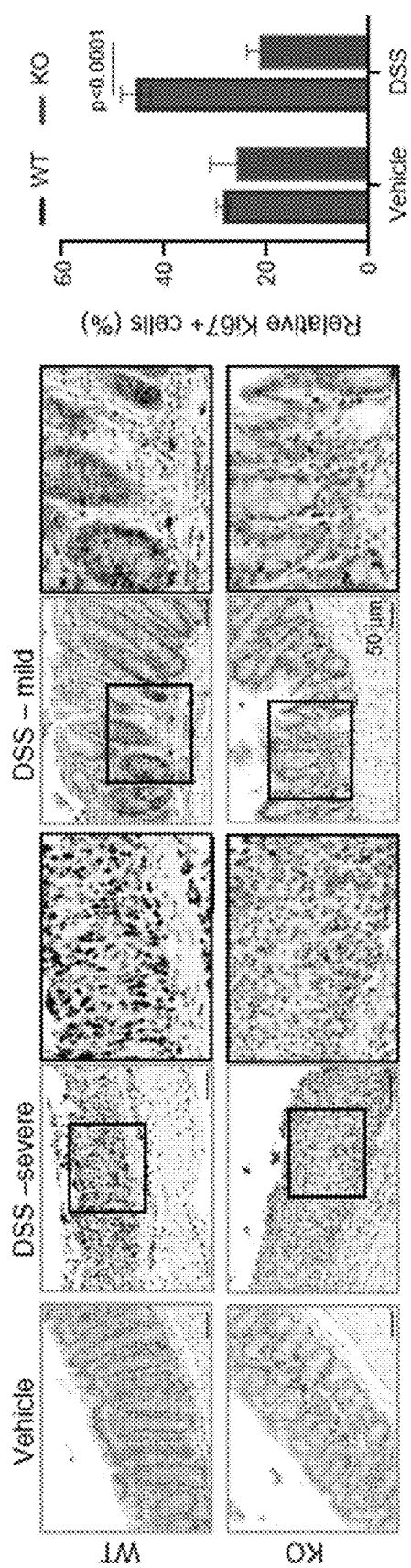
FIGS. 9A to 9D show a test for confirming a degree of removal of apoptotic cells in NAMPT-knocked out macrophages.
Figure 9B:
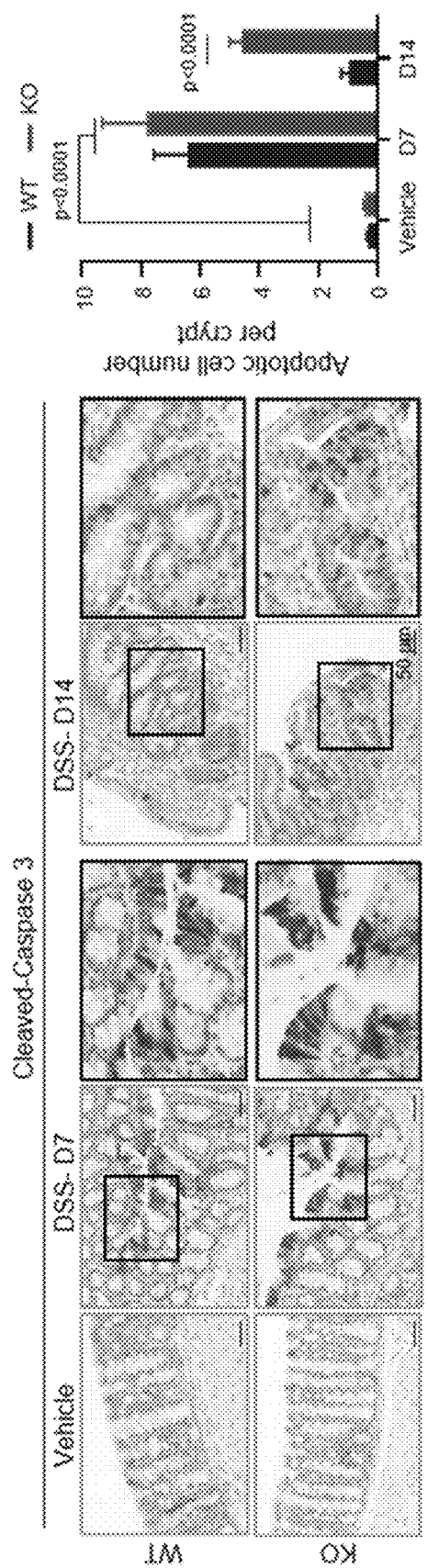
Figure 9C:
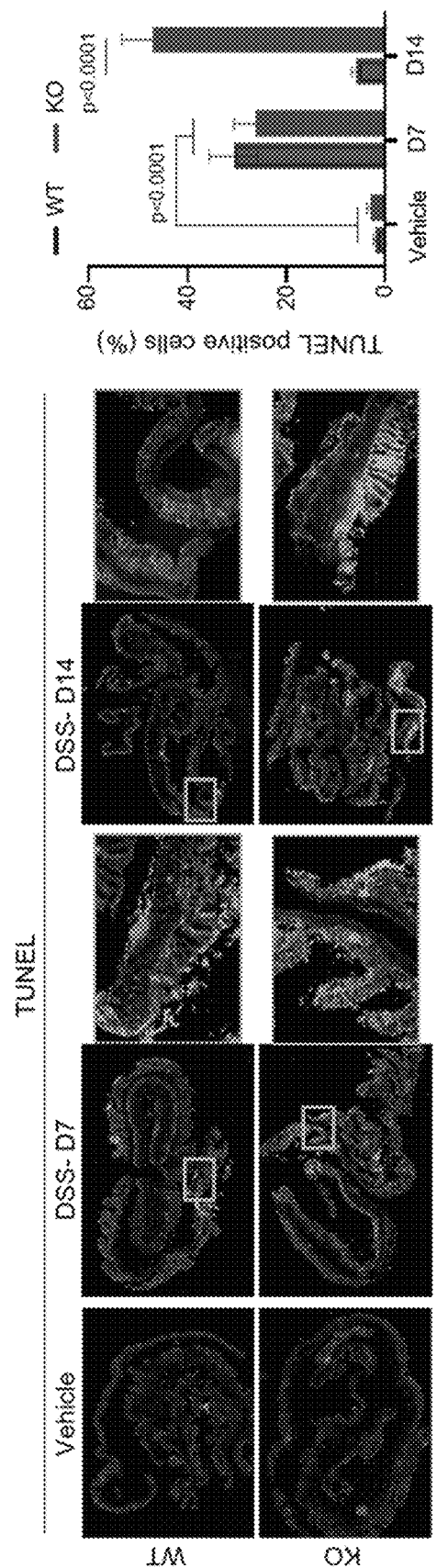

[Experimental Example 5] Confirmation of Whether NAMPT Knock Out Inhibits Apoptotic Cell Removal in DSS-Induced Colitis As an index of tissue damage recovery, Ki67$^+$ cells were measured in DSS-induced colitis samples from WT mice and KO mice on day 7. As a result, according to FIG. 9A, the proportion of Ki67$^+$ cells in the epithelium was extremely decreased in KO mice. To investigate the role of NAMPT in removing apoptotic cells in vivo, colon tissues of WT mice and KO mice with DSS-induced colitis were stained with cleaved caspase 3 antibody to see remaining apoptotic cells. As a result, according to FIGS. 9B and 9C, it was confirmed that the number of unremoved apoptotic cell corpses was greatly increased in KO mice on day 14, and it was confirmed that the number of tunel-positive (TUNEL$^+$) nuclei in the colonic epithelium and mucosa of KO mice was significantly increased compared to WT mice.

Figure 9D:
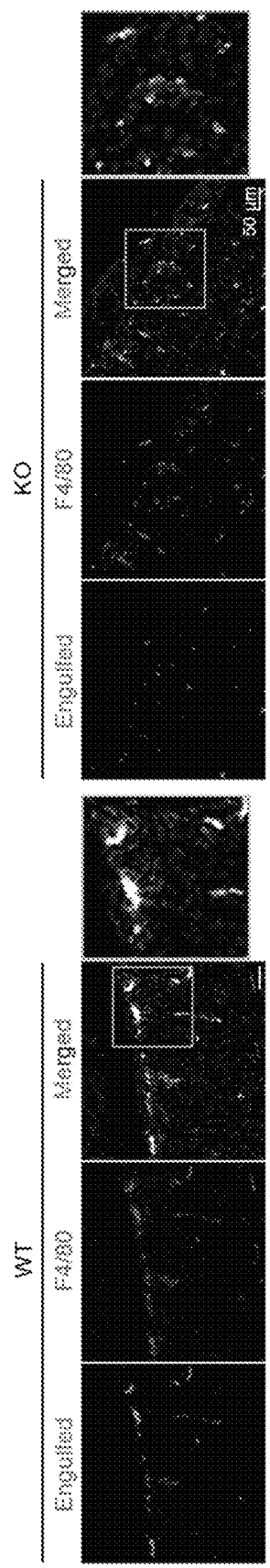

In the DSS-induced colitis model, whether NAMPT knocked out macrophages exhibit reduced phagocytosis was confirmed using a detection method capable of distinguishing phagocytosed cells within phagocytes. As a result, according to FIG. 9D, the signal of phagocytosed cells was higher in WT mice than in NAMPT KO mice. In addition, it was confirmed that F4/80$^+$ macrophages exhibited lower levels of phagocytosed cells in the colon tissue of KO mice.

Therefore, it was found that the knock out of NAMPT in activated inflammatory macrophages can attenuate the cell removal activity and eventually increase the severity of colitis.

Figure 10A:
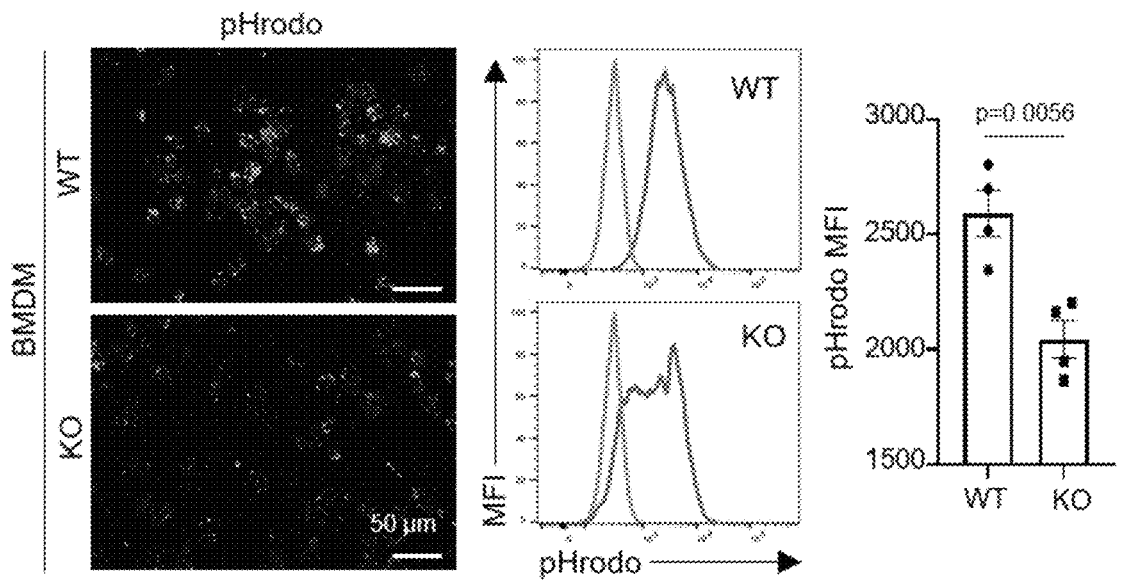
FIGS. 10A to 10H show a test for confirming whether NAMPT expression in macrophages necessarily affects phagocytic activity.
Figure 10B:
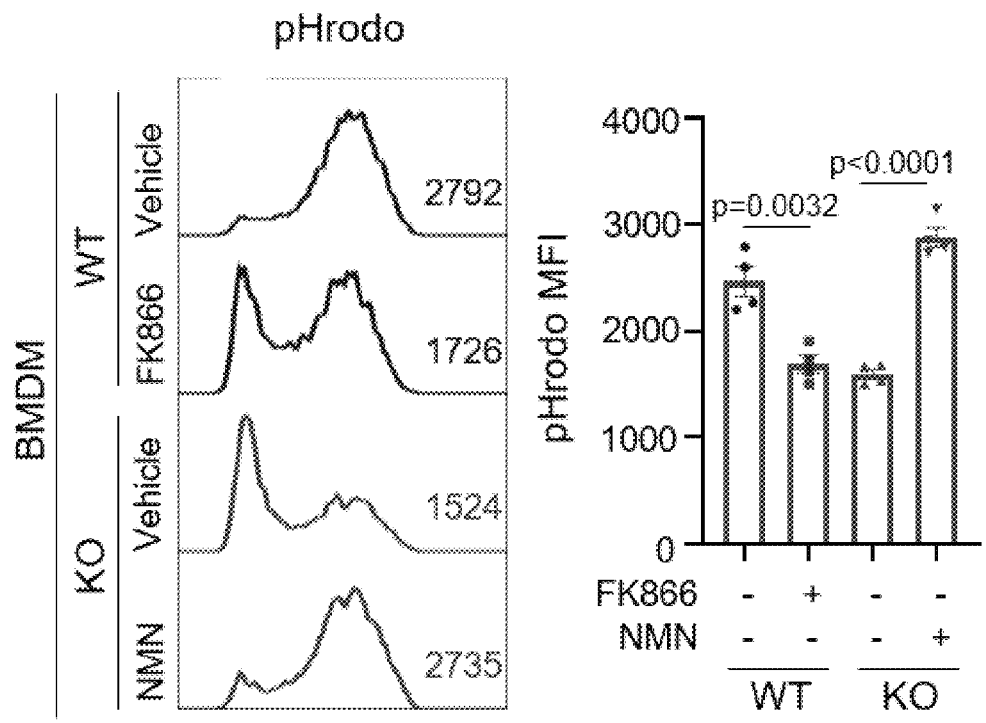
Figure 10C:
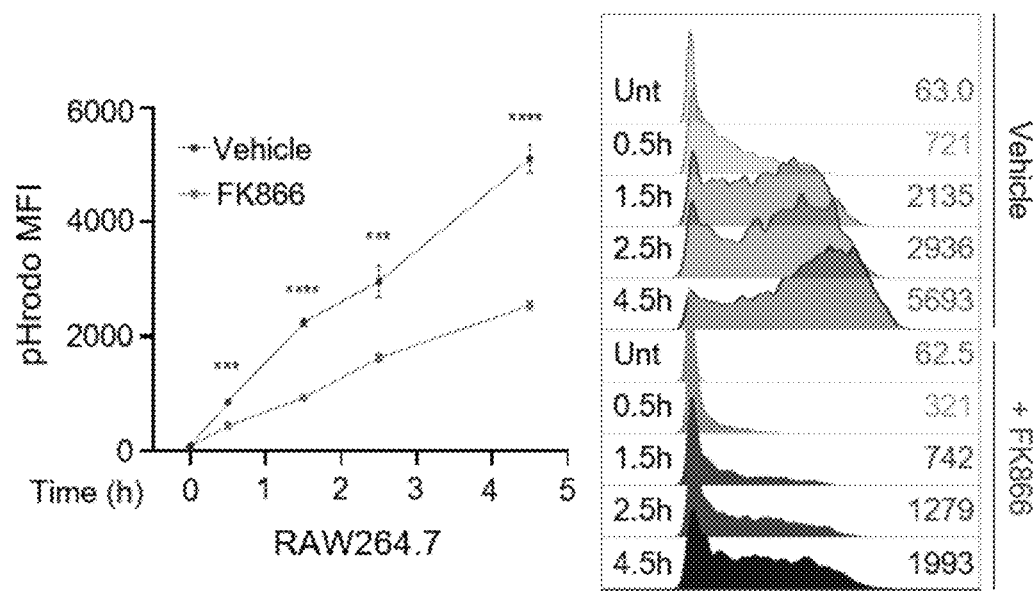
Figure 10D:
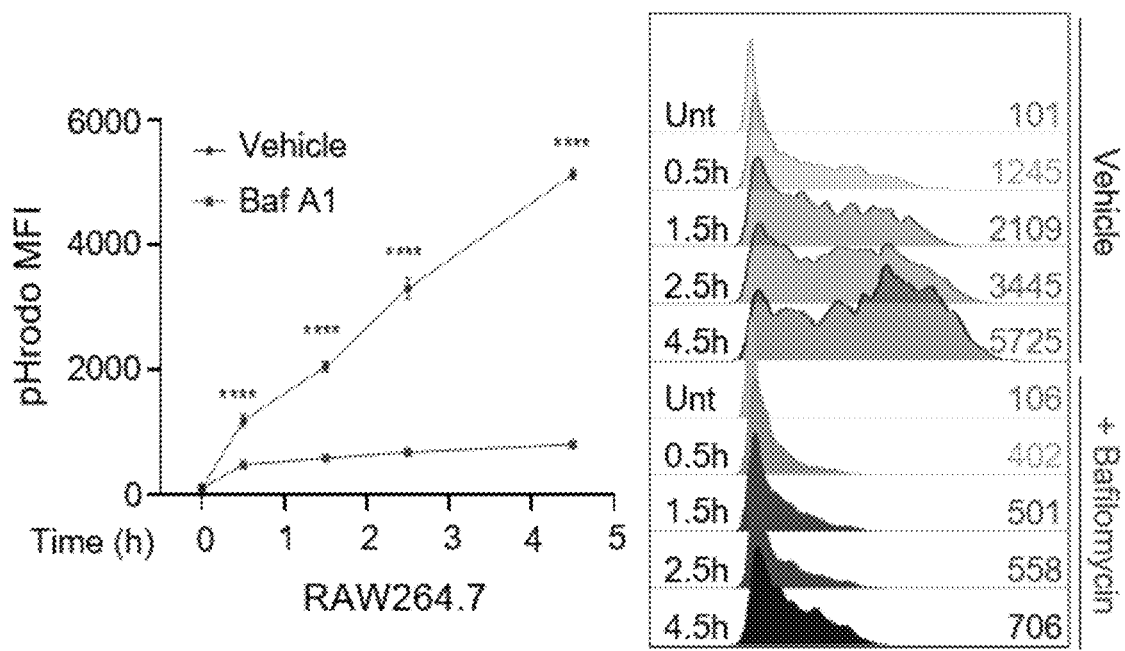
Figure 11A:
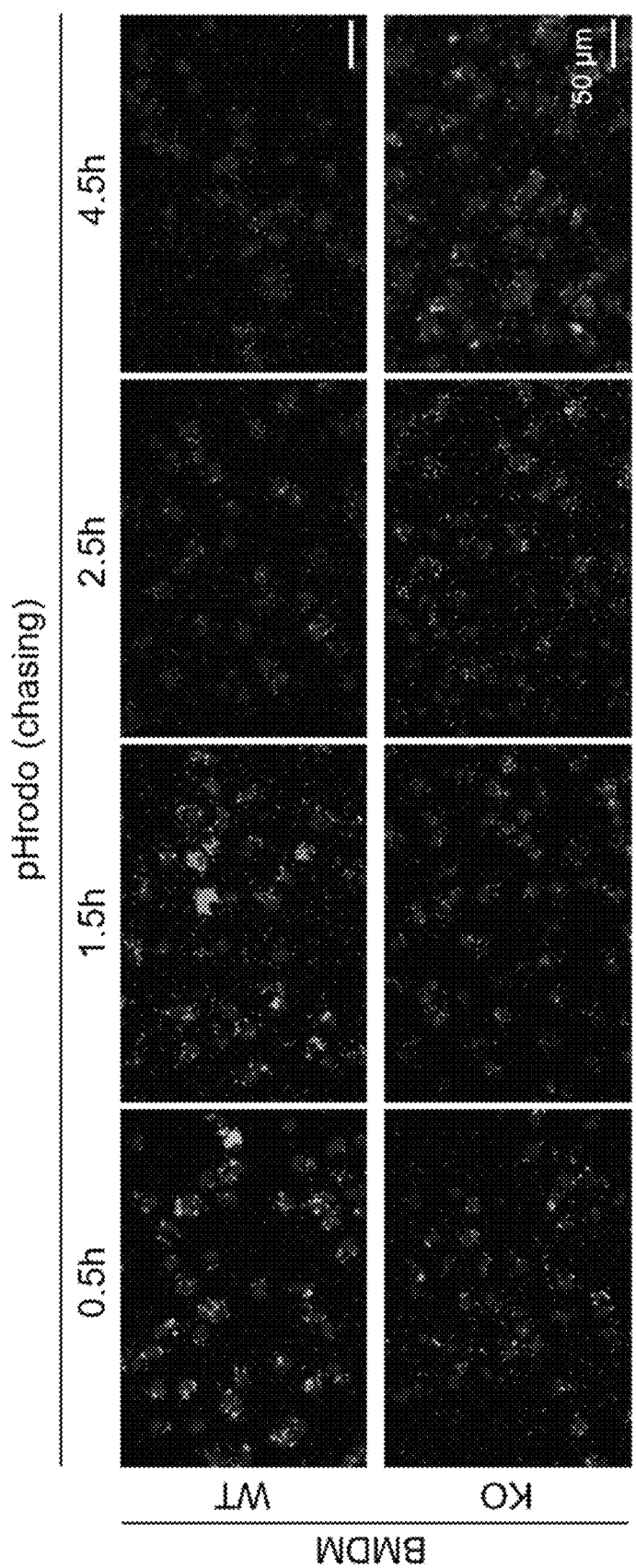
FIGS. 11A to 11D show a test for confirming whether NAMPT promotes phagocytosis.
Figure 11B:
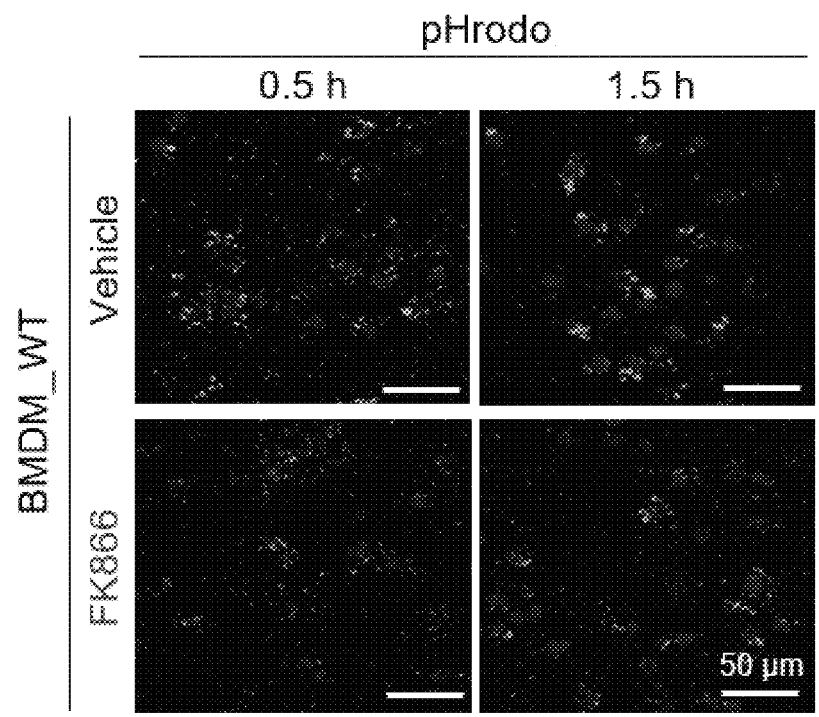
Figure 11C:
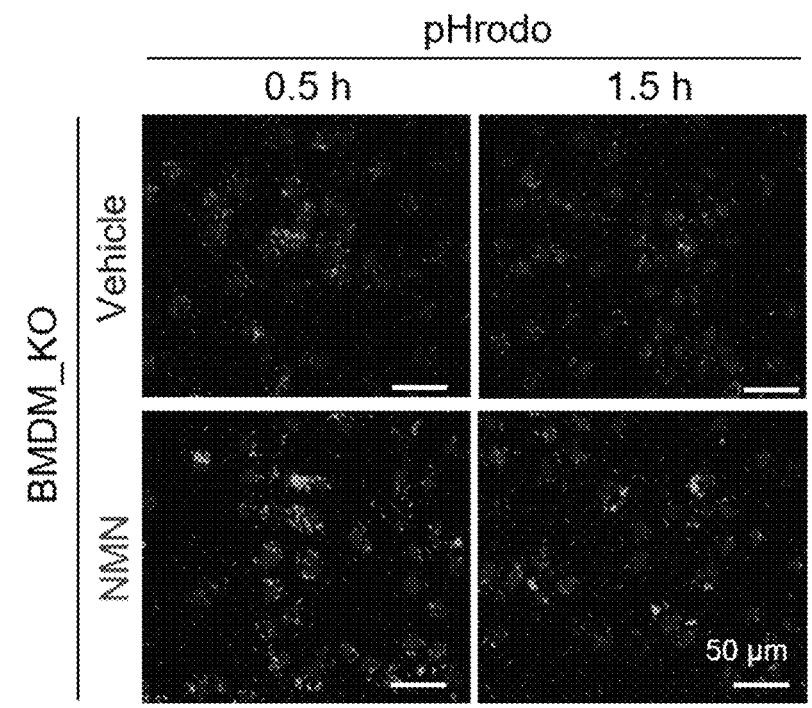
Figure 11D:
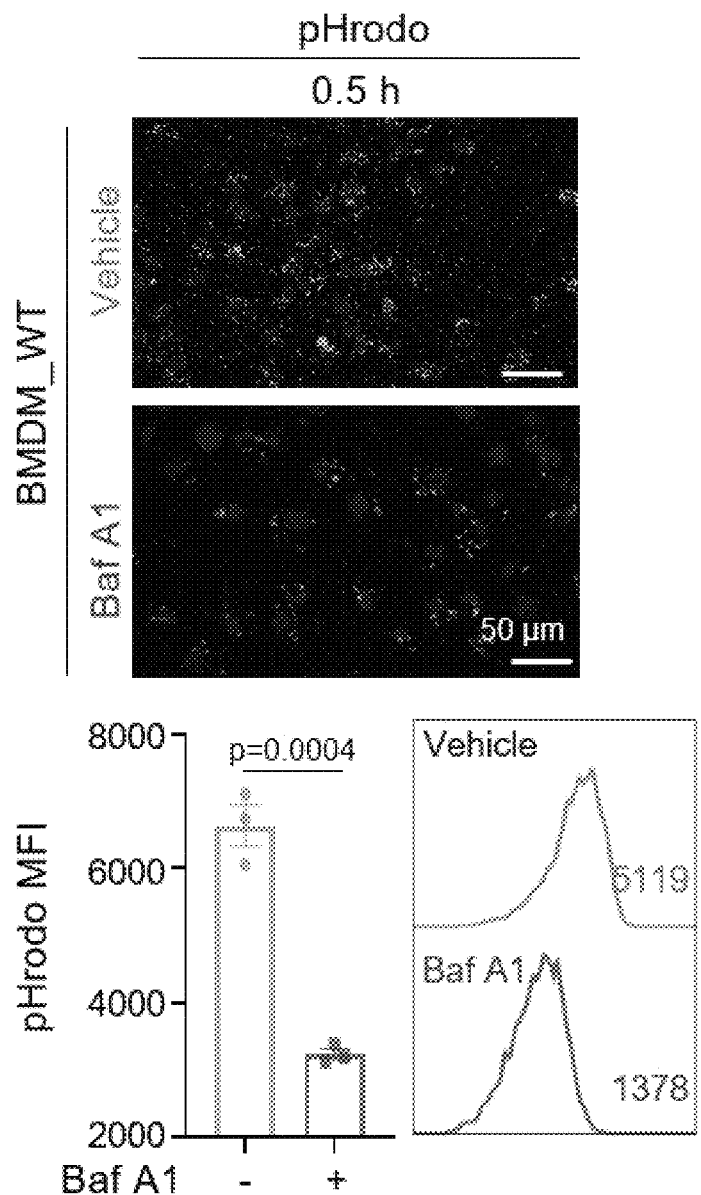

[Experimental Example 6] Confirmation of Attenuated Phagocytic Activity in NAMPT Knocked Out Macrophages Pulse and chase phagocytosis assays were performed using pHrodo green to compare phagocytic activity between macrophages of WT and KO mice. In FIG. 11A, there was an increase in the intensity of the green fluorescence signal in the BMDM of WT mice, indicating the gradual maturation and fusion of phagosomes containing pHrodo green with lysosomes. As in Experimental Example 4, while there was no difference in BMDM polarization during LPS/IFN-γ treatment, according to FIG. 10A, it was confirmed that the green fluorescence intensity significantly decreased in BMDM of KO mice compared to BMDM of WT mice when treated with pHrodo for 30 minutes. When FK866 was treated in BMDM of WT mice, according to FIG. 10B, FIG. 11B and FIG. 11C, the pHrodo intensity decreased, and it was confirmed that nicotinamide mononucleotide (NMN) treatment restored fluorescence intensity in BMDM of KO mice. Inhibition of NAMPT activity by FK866 reduced pHrodo intensity in RAW264.7 cells, as shown in BMDM of WT mice, according to FIG. 10C. According to FIG. 10D and FIG. 11D, treatment with the lysosomal inhibitor bafilomycin A1 (Baf A1) reduced the fluorescence intensity of pHrodo in both BMDM and RAW264.7 cells from WT mice, which means that the phagocytosed pHrodo green $E.\ coli$ bioparticles were degraded in macrophages, and these results indicate that the enzymatic activity of NAMPT promotes phagocytic progression in macrophages.

Figure 10E:
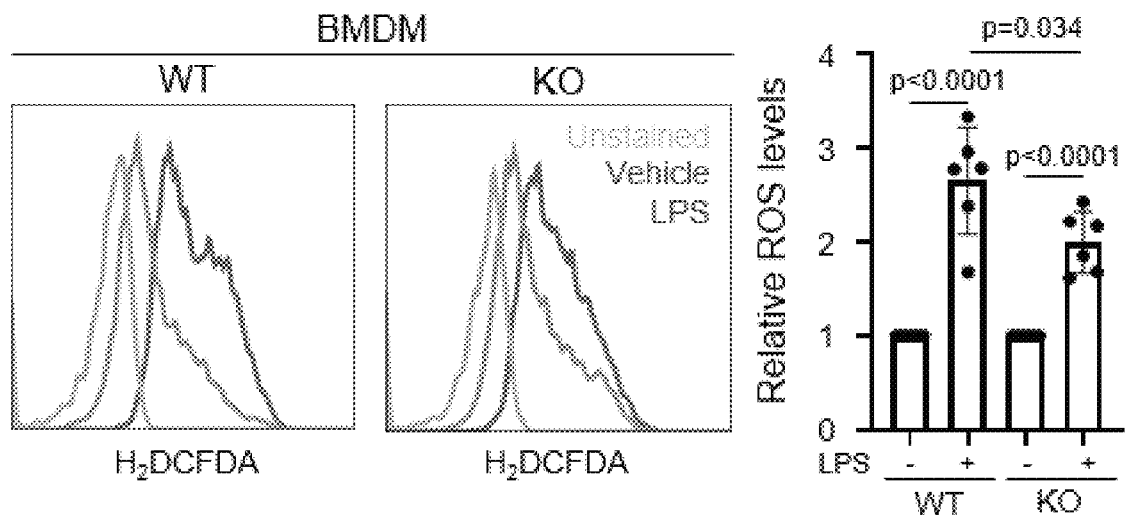
Figure 10F:
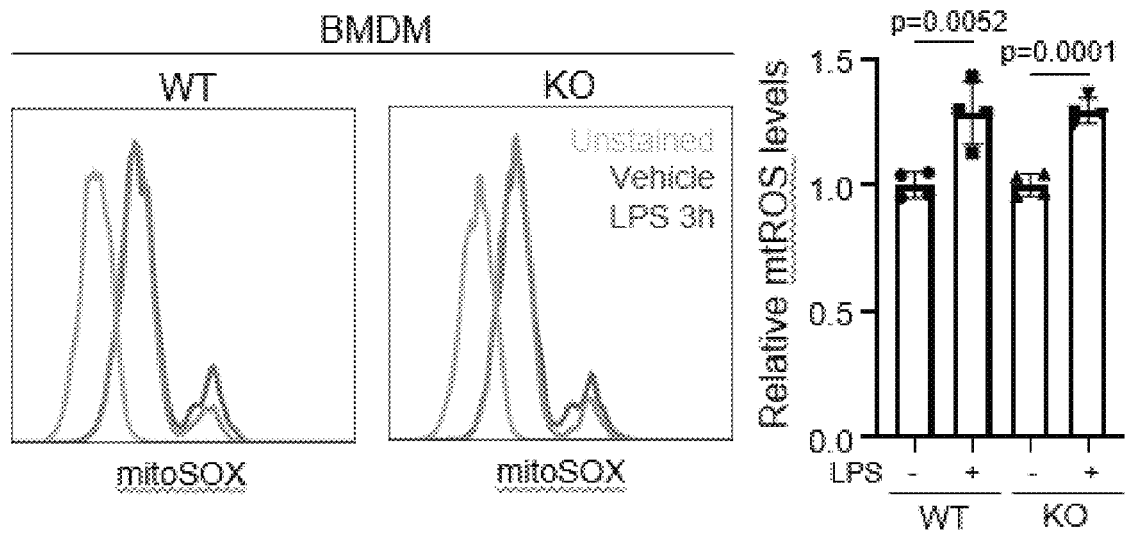
Figure 10G:
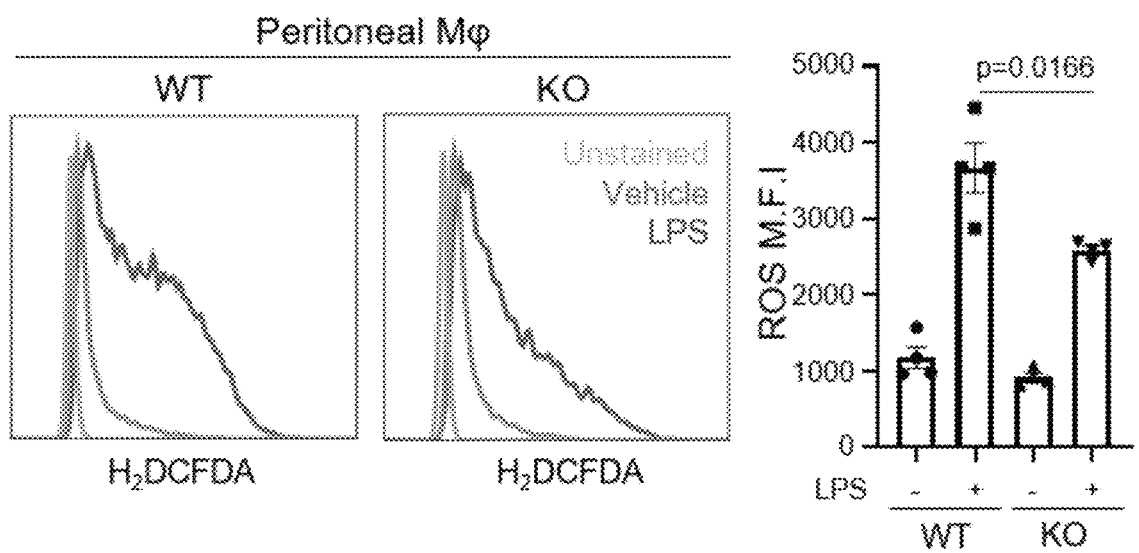
Figure 10H:
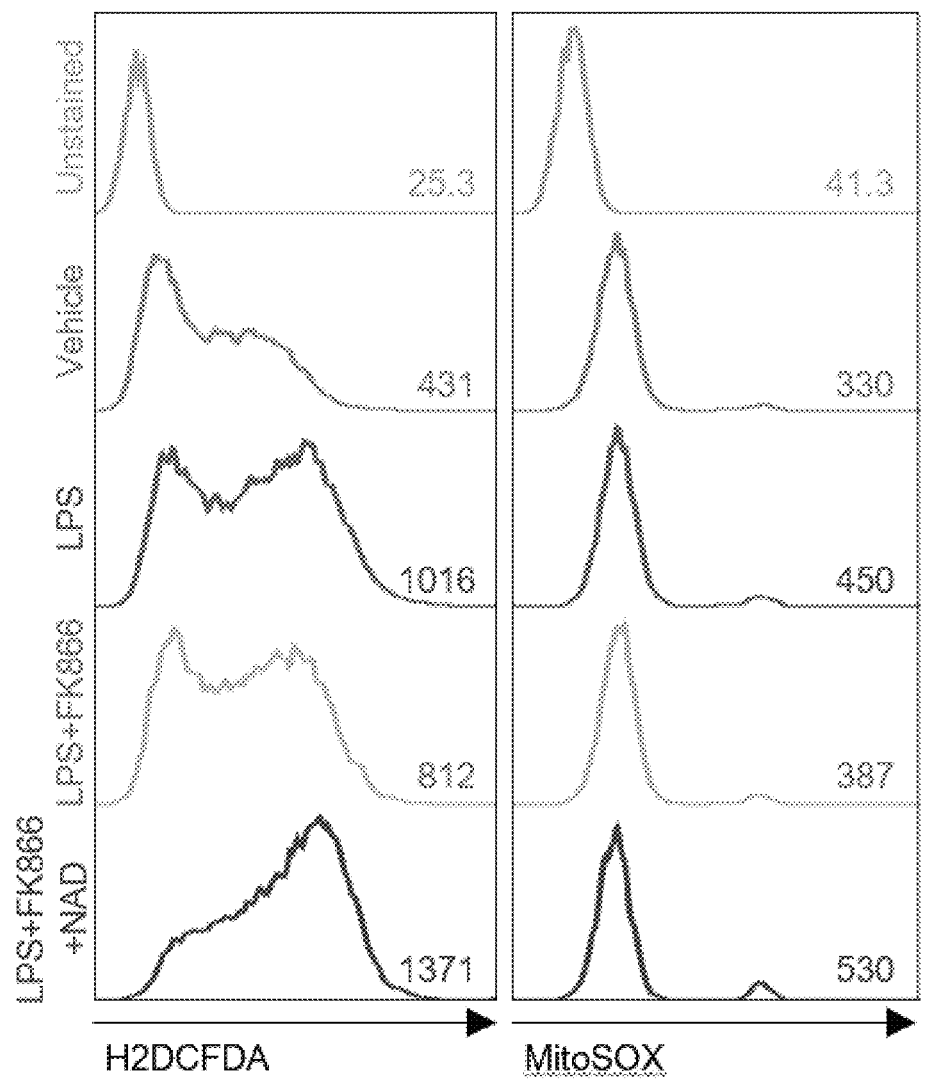

ROS levels were measured in BMDM of KO mice and WT mice upon LPS treatment. As a result, according to FIGS. 10E, 10G and 10F, NAMPT-knocked out BMDM and peritoneal macrophages exhibited defects in cellular ROS production upon LPS treatment, and unlike total cellular ROS levels, mitochondrial ROS levels upon LPS treatment were not statistically significantly different between macrophages of WT mice and KO mice. In addition, the response to LPS according to FK866 treatment was confirmed in Raw 264.7 cells, and according to FIG. 10H, ROS production was partially inhibited, and this inhibitory effect was recovered by $NAD^+$ co-treatment. These results showed that NAMPT expression in macrophages promotes phagocytic activity in an enzyme-dependent manner.

Figure 12A:
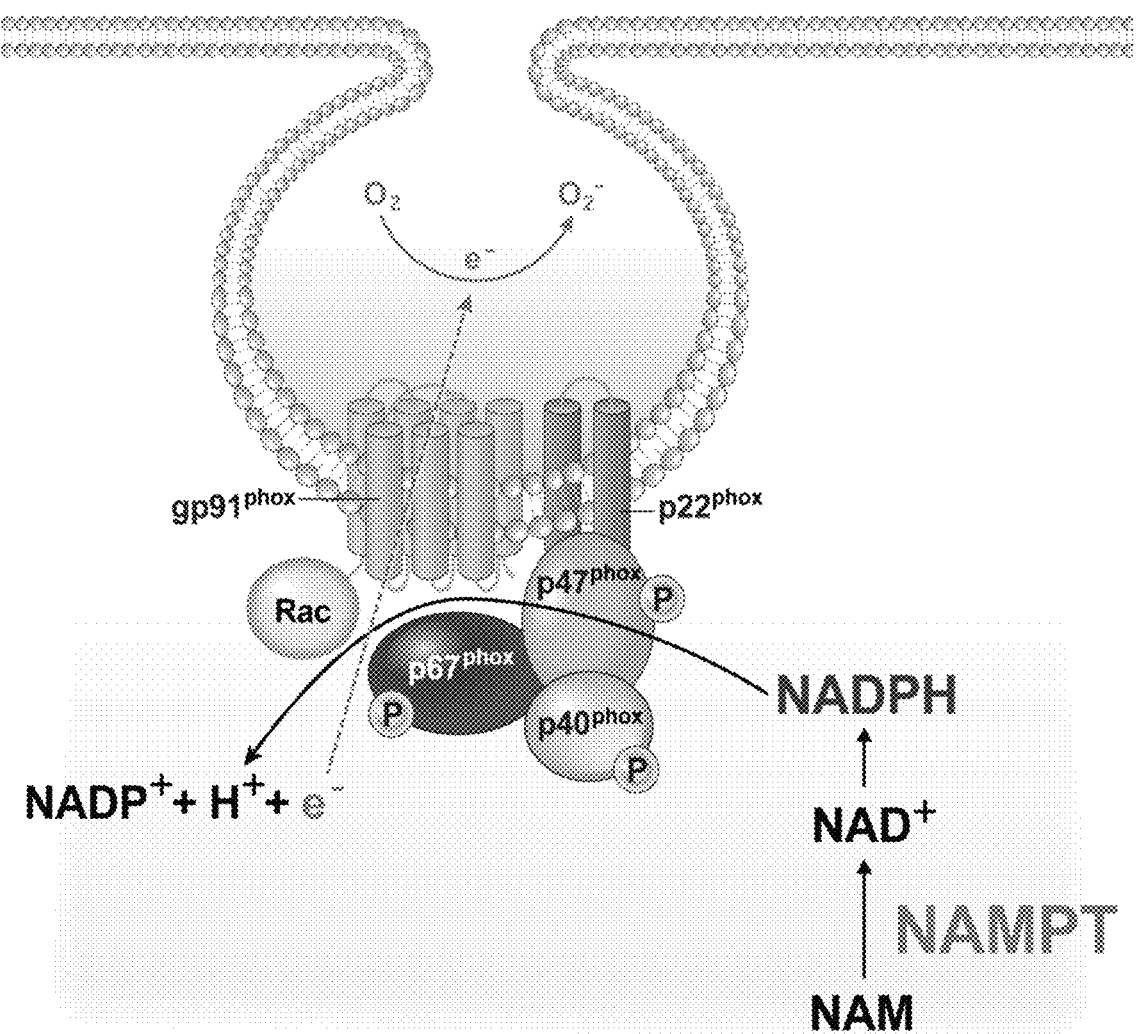
FIGS. 12A to 12J show a test for confirming whether NAMPT level is increased through a pentose phosphate pathway (PPP).
Figure 12B:
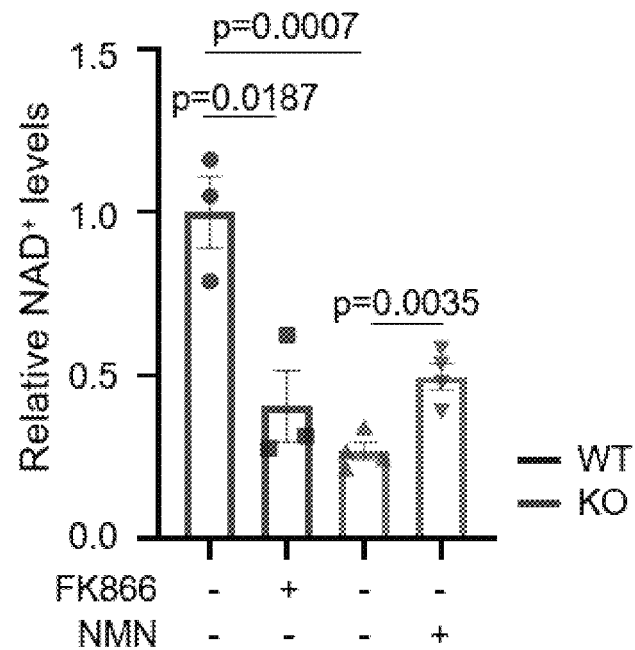
Figure 12C:
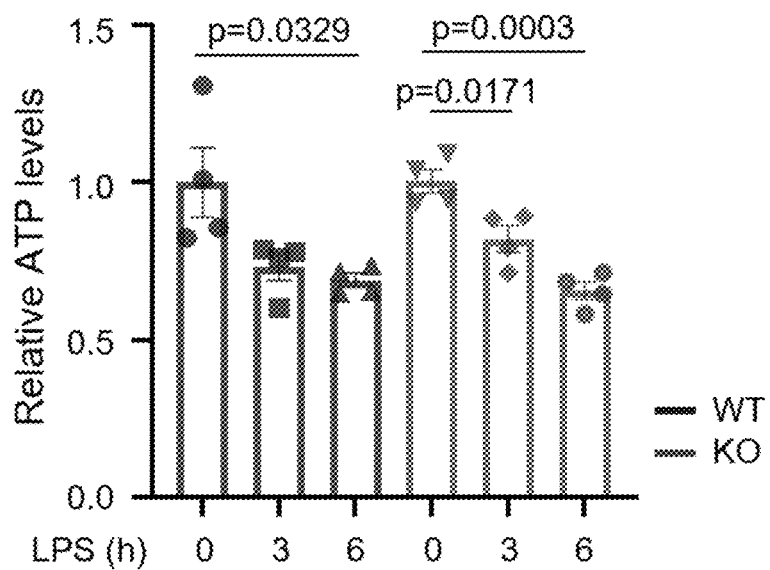
Figure 12D:
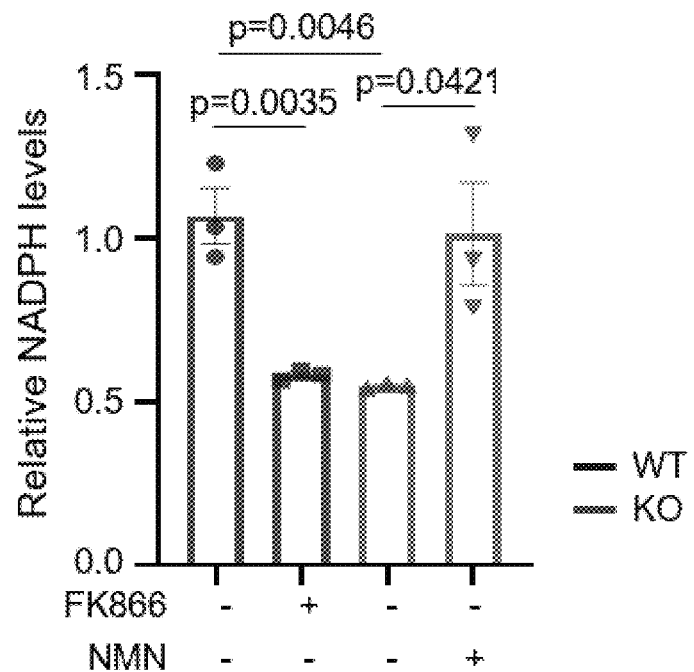
Figure 12E:
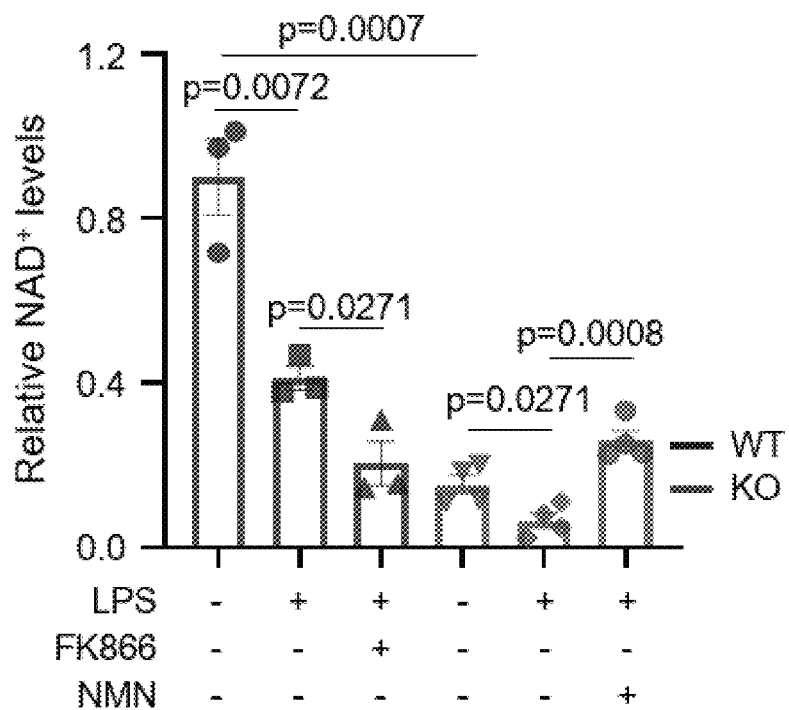
Figure 12F:
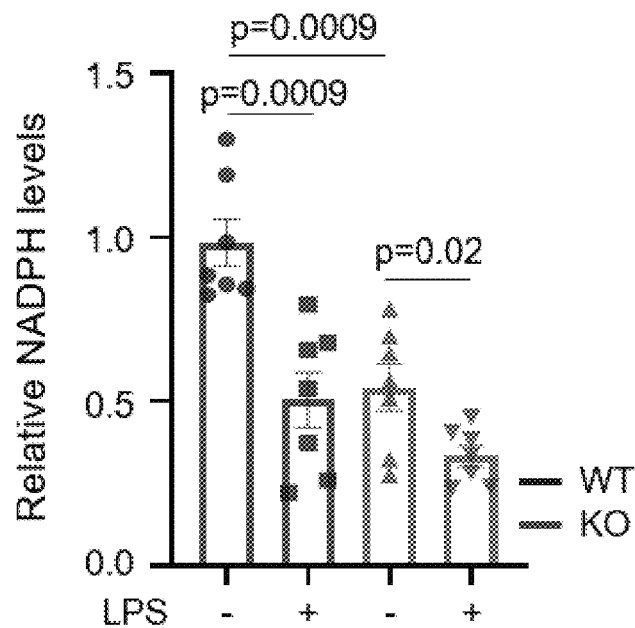
Figure 12G:
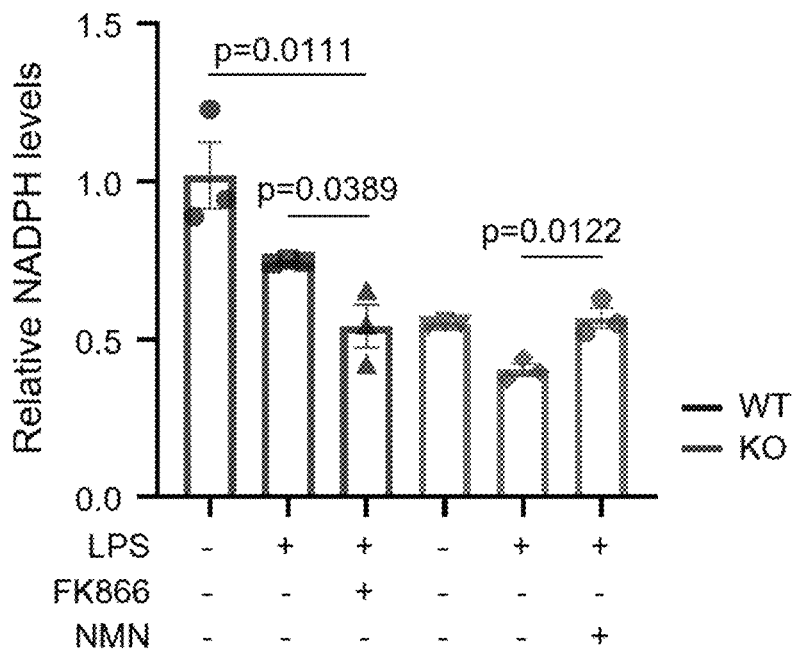

[Experimental Example 7] Confirmation of $NAD^+$ Generation for Phagocytic Activity of NAMPT Knocked Out Macrophages Macrophages require NADPH as an electron carrier for ROS production, and it was assumed that, as shown in FIG. 12A, macrophages knocked out of NAMPT exhibit defective phagocytic activity due to reduced NADPH levels. As expected, according to FIG. 12B, it was confirmed that NAMPT knock out or FK866 treatment significantly reduced $NAD^+$ levels, and NMN treatment restored the phenotype. Since $NAD^+$ is an important cofactor in ATP production, ATP levels were measured during LPS treatment. As a result, according to FIG. 12C, LPS reduced ATP levels in both BMDMs from KO mice and WT mice, while there was no difference in ATP levels under vehicle treatment between BMDMs from KO mice and WT mice, which suggests that NAMPT is not directly involved in ATP production in the immune response. In addition, according to FIGS. 12D and 12E, NADPH levels were down-regulated in macrophages of KO mice, and NMN administration increased NADPH levels, which suggests that NAMPT enzyme activity regulates NADPH levels in BMDM, LPS treatment reduces $NAD^+$ levels, and FK866 treatment causes a further decrease. Consistently, the LPS challenge significantly reduced NADPH levels to 50% in macrophages of WT mice. However, the NADPH level in NAMPT-depleted macrophages was reduced by 21%. In addition, according to FIG. 12G, FK866 treatment caused a further decrease in NADPH levels, while NMN treatment increased NADPH levels in LPS treatment. Therefore, these results confirmed that NAMPT-depleted macrophages could not sufficiently produce NADPH, an important factor in the immune response.

Figure 12H:
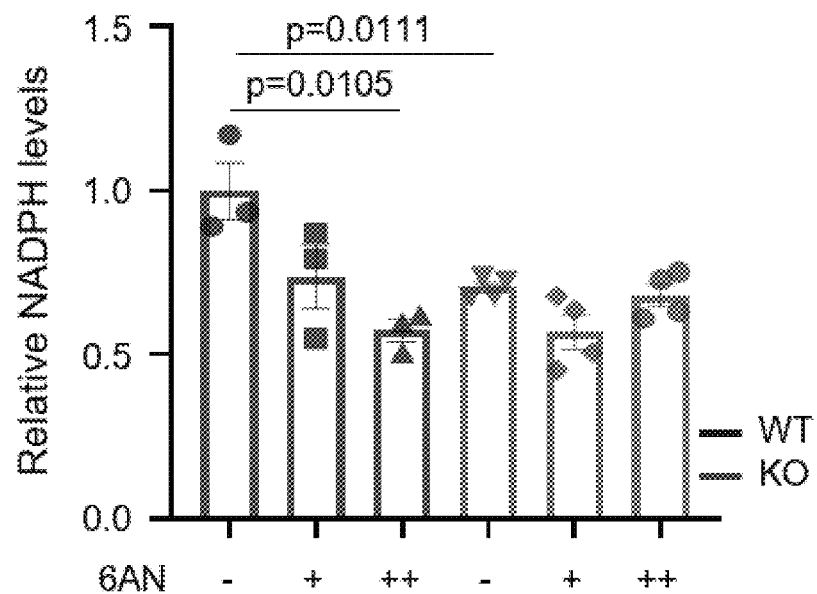
Figure 12I:
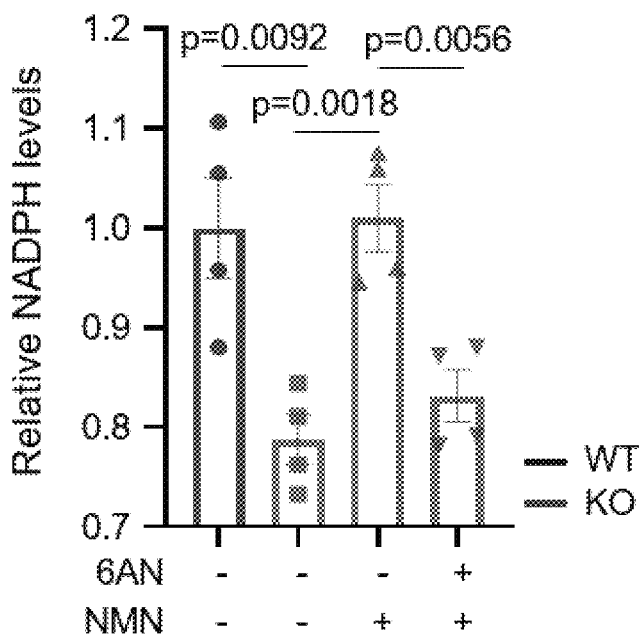
Figure 12J:
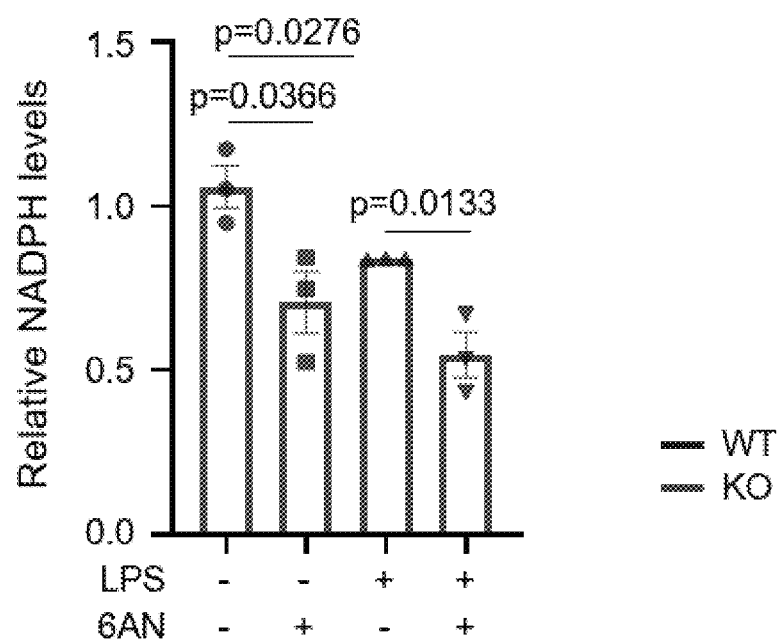
Figure 13A:
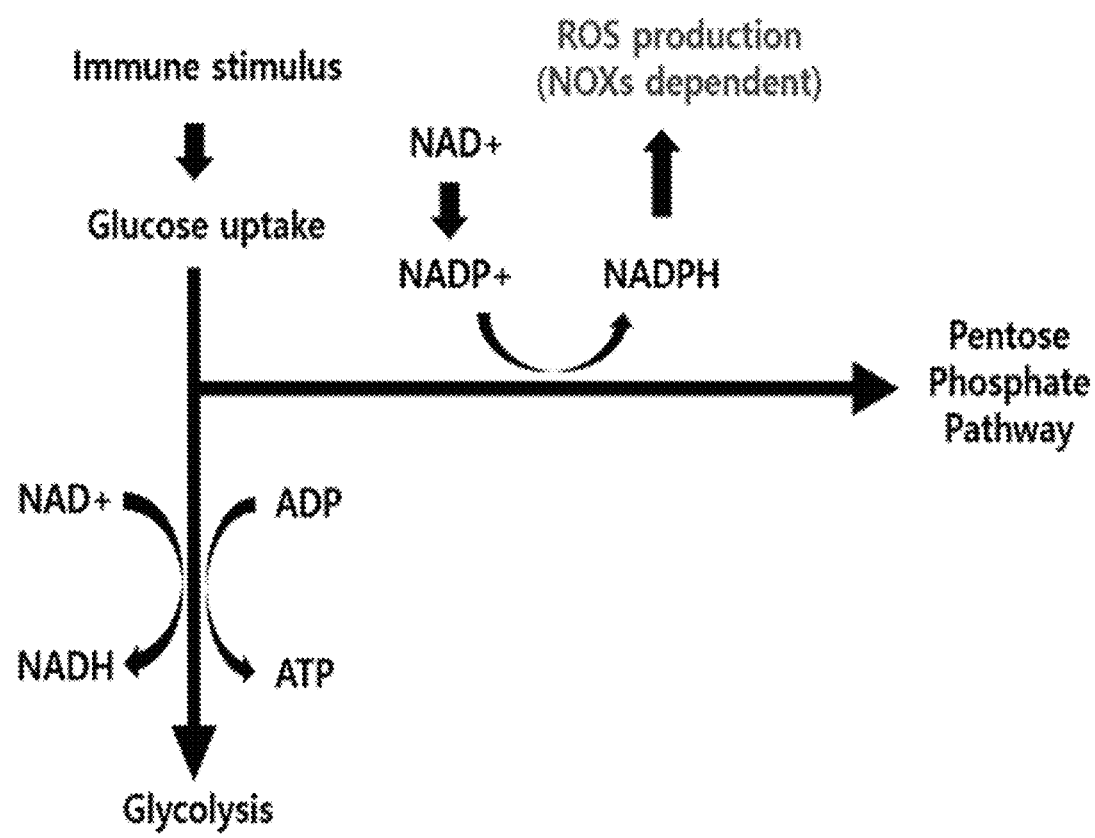
FIGS. 13A and 13B show a test for confirming whether NAMPT level is increased through PPP to increase reactive oxygen species (hereinafter, referred to as ROS) levels.
Figure 13B:
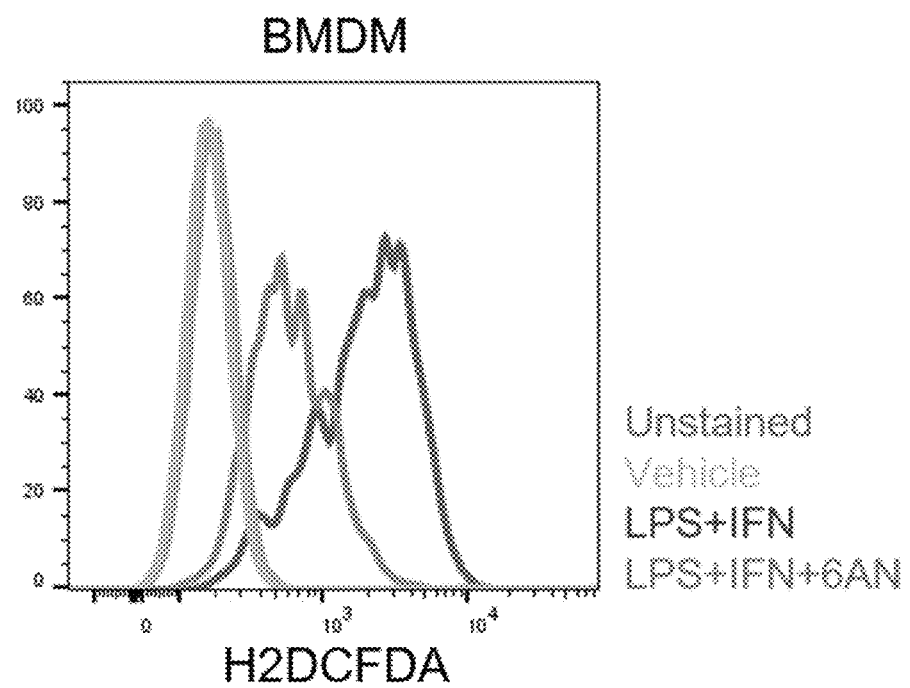

NAMPT promotes NADPH production by increasing the influx of $NAD^+$ into the pentose phosphate pathway (PPP), and according to FIG. 13A and FIG. 12H, it was found that oxidative burst requires a large amount of NADPH to feed the production of peroxide through NOX2, and while treatment with 6-aminonicotinamide (hereinafter, referred to as 6AN), which inhibits PPP, reduced NADPH levels in a dose-dependent manner in WT mice, but not in macrophages from KO mice. In addition, according to FIG. 12I, FIG. 12J and FIG. 13B, it was confirmed that NMN treatment restored NADPH levels in macrophages of KO mice that were blocked by 6AN treatment, and inhibition of PPP by 6AN during LPS challenge further reduced NADPH levels, and as expected, 6AN treatment led to a decrease in ROS levels in LPS- and IFN-γ-activated BMDMs. Therefore, these results suggest that NAMPT promotes NADPH production through PPP to supply material to NOX2 in the context of phagocytosis.

[Experimental Example 8] Confirmation of NMN Administration Effect

In order to determine whether the effects of NAMPT knock out on colitis could be mitigated by NMN supplementation, NMN was administered in a DSS-induced colitis model. After treatment with 2.5% DSS, 500 mg/kg of NMN or PBS was intraperitoneally injected into NAMPT KO mice 3 times a week, and according to FIG. 14A, FIG. 14B, FIG. 15A and FIG. 14C, survival rates showed that NMN treatment protected KO mice from severe colitis and restored weight loss and DAI reduction, wherein PBS injection showed 33% survival (4 out of 12), whereas NMN injection showed 67% survival (8 out of 12). It was further elucidated whether there was any clear cytotoxic effect by NMN injection in mice. As a result, according to FIG. 15B, FIG. 14D, FIG. 15C, and FIG. 14E, NMN injection did not result in weight loss until around 14 days after administration, there were no abnormalities in the colon, liver and spleen at the microscopic level, and serum ALT and AST levels were similar between the PBS and NMN treatments. These results suggest that NMN injection may attenuate DSS-induced colitis without hepatotoxicity.

Figure 14A:
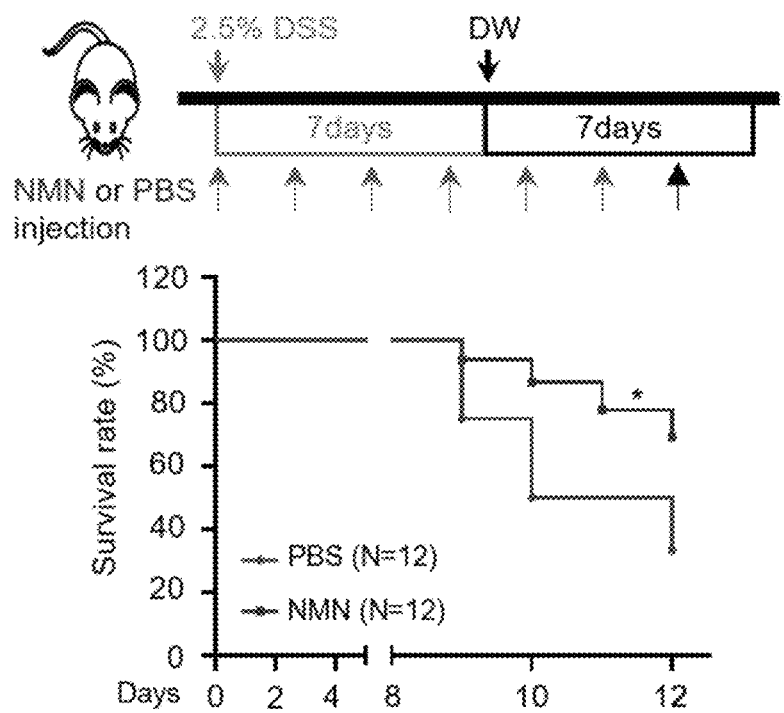
FIGS. 14A to 14F show a test for confirming whether administration of nicotinamide mononucleotide (hereinafter referred to as NMN) improves severity of DSS-induced colitis.
Figure 14B:
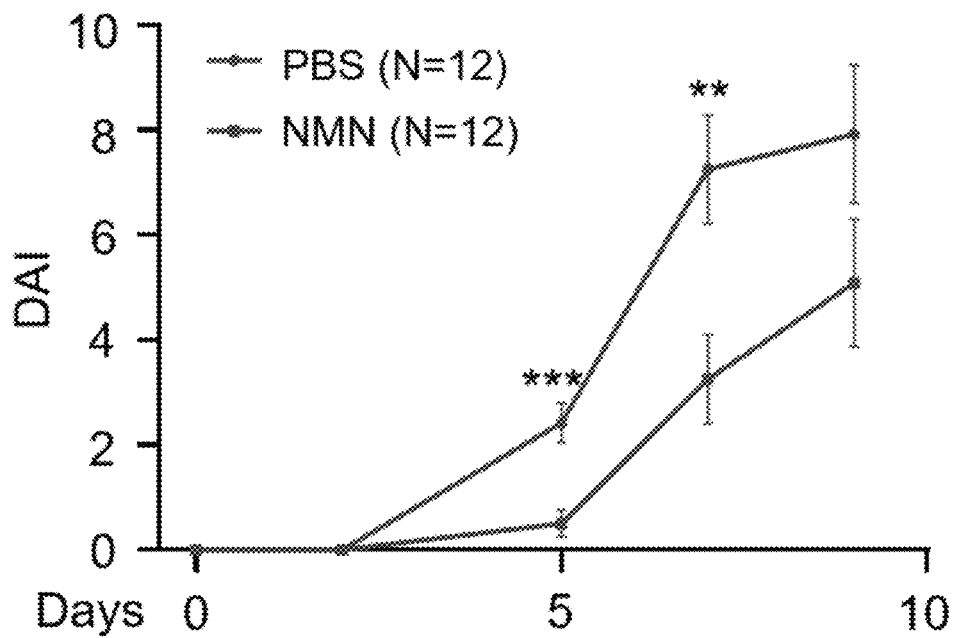
Figure 14C:
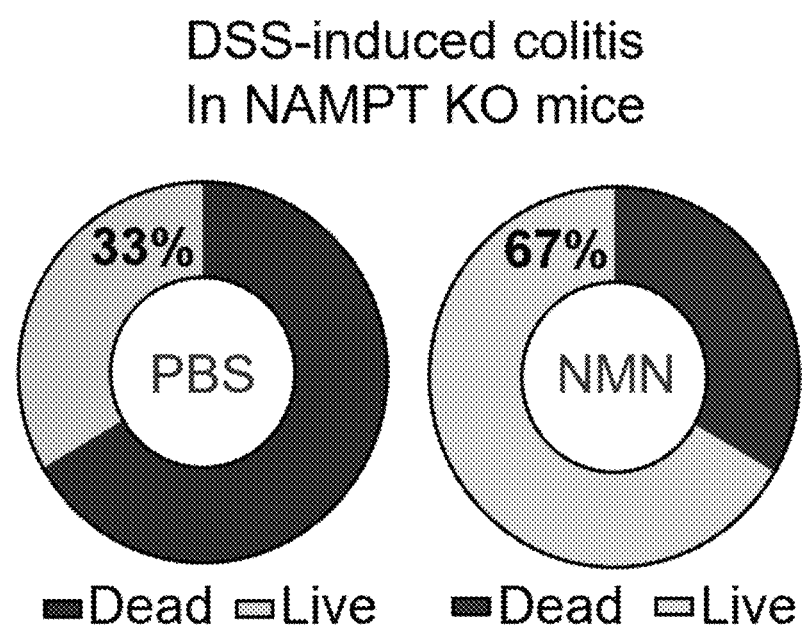
Figure 14D:
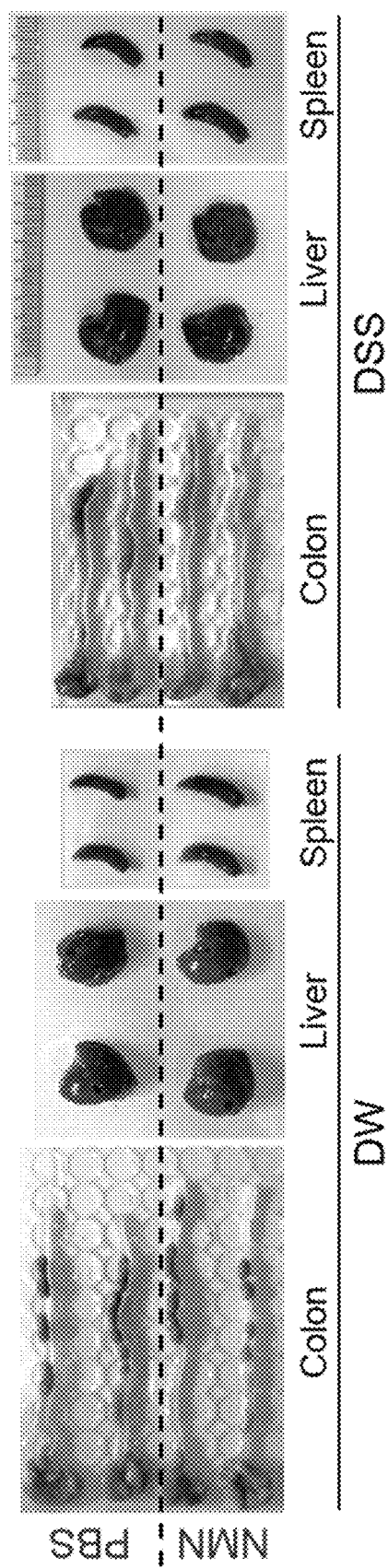
Figure 14E:
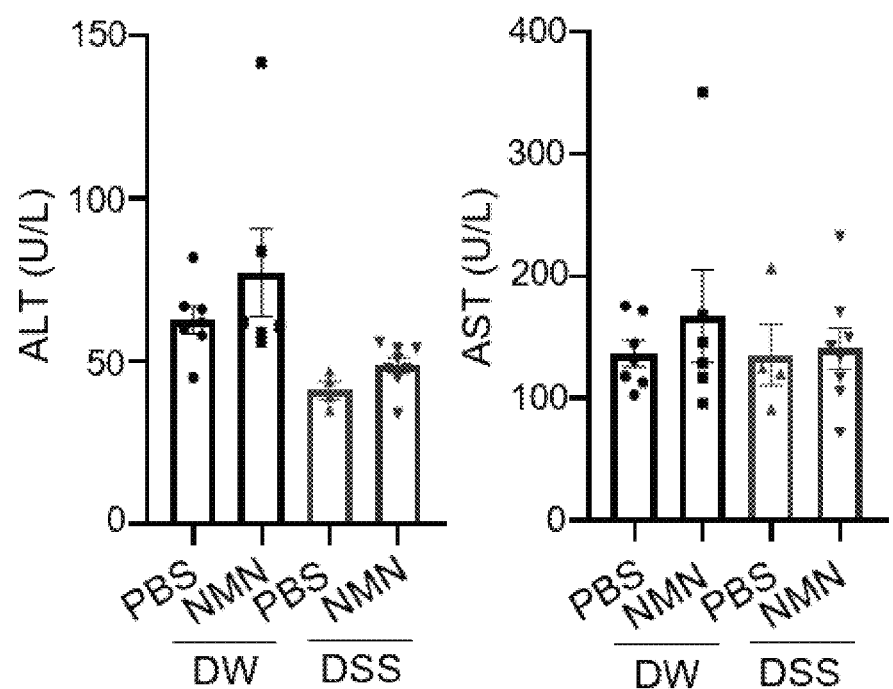
Figure 14F:
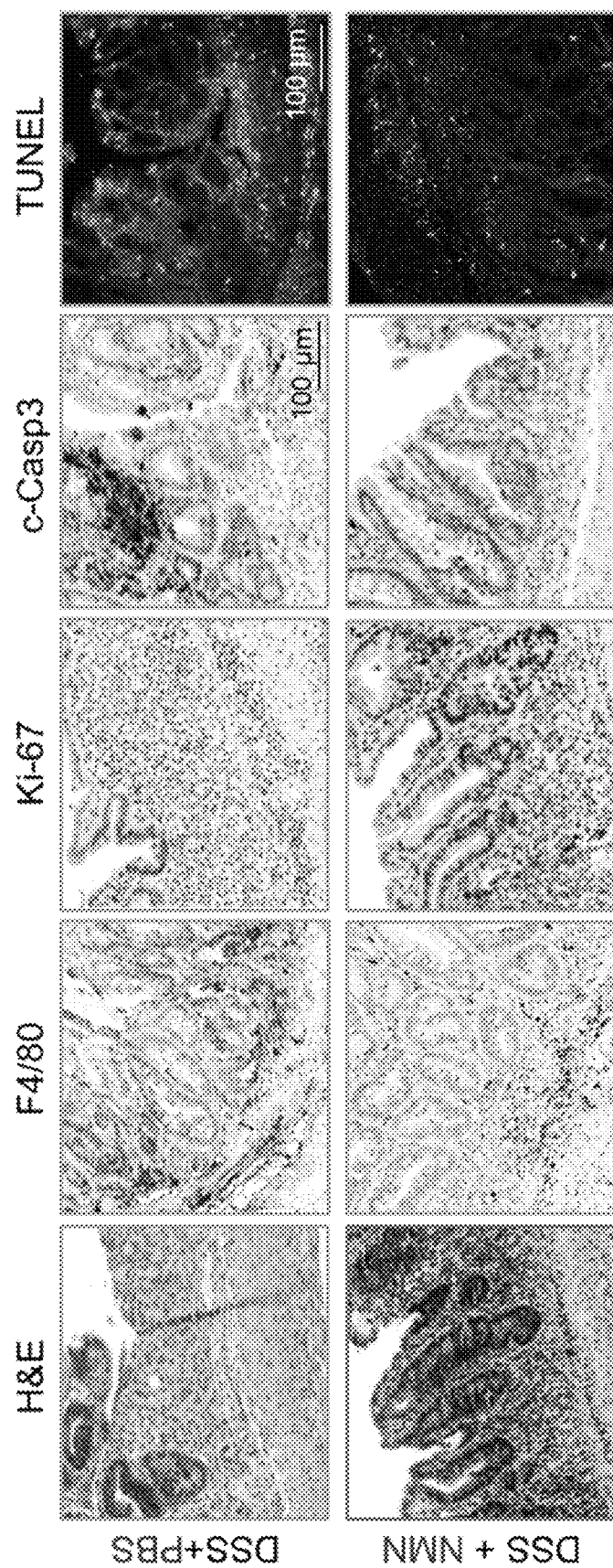
Figure 15A:
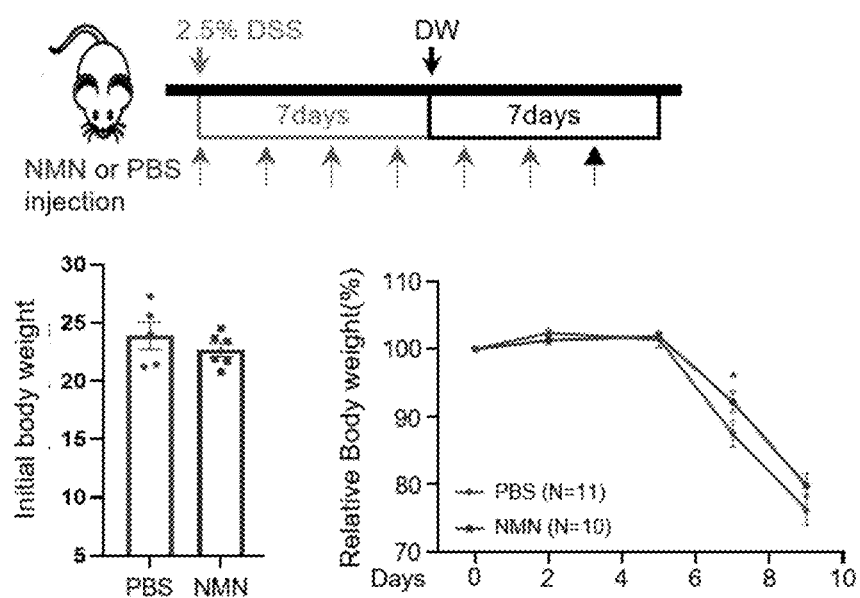
FIGS. 15A to 15C show a test for confirming whether administration of NMN relieves inflammation of DS S-induced colitis.
Figure 15B:
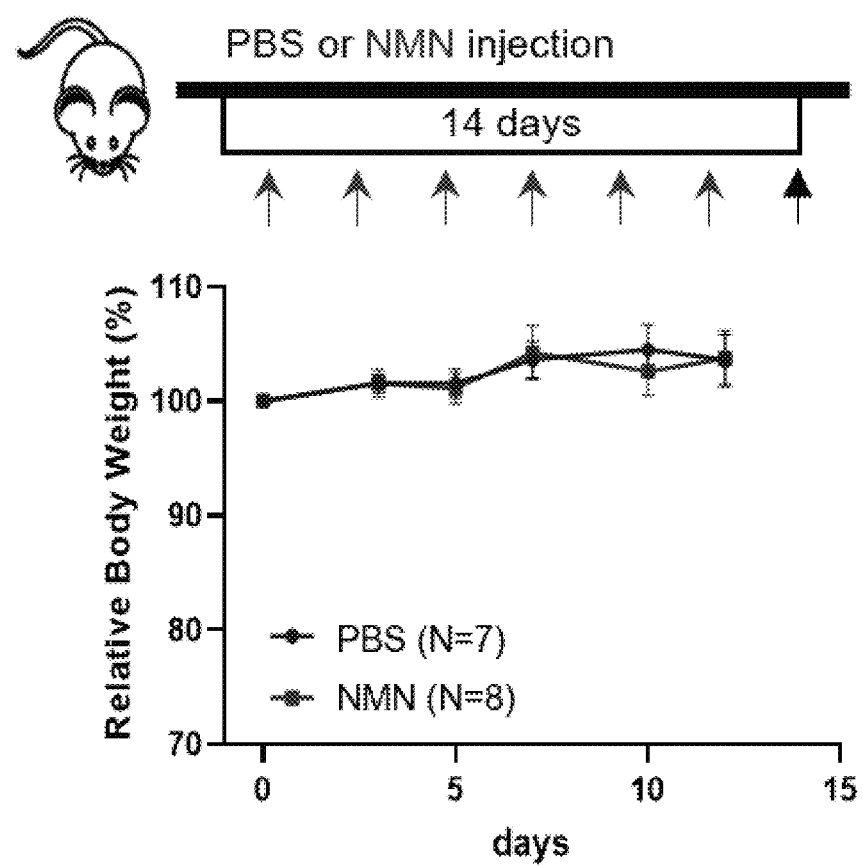
Figure 15C:
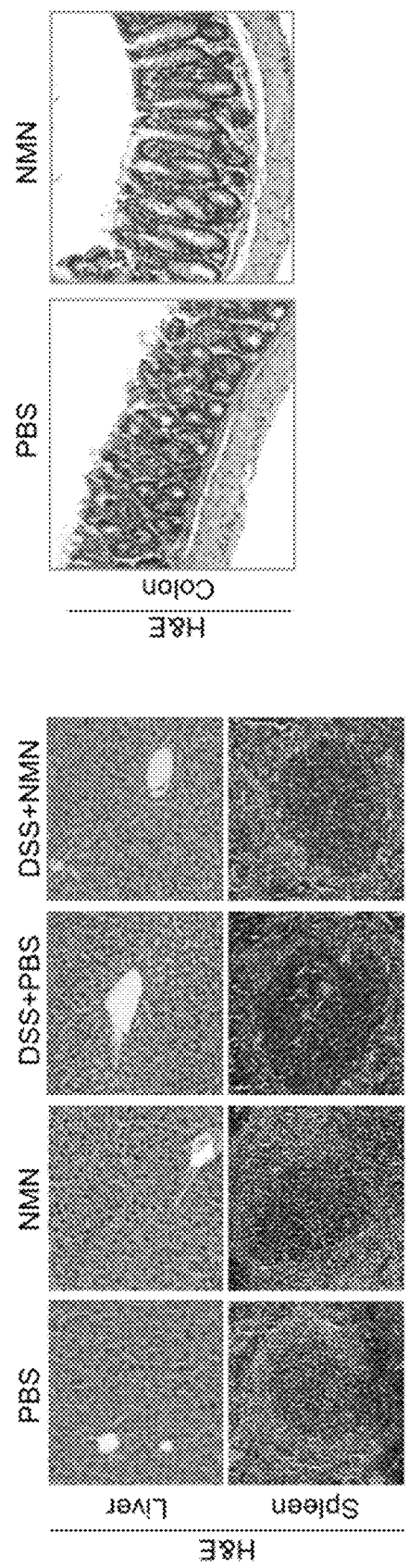

Also, according to FIG. 14F, NMN treatment increased $Ki-67^+$ cells and decreased positive signals of cleaved caspase 3 and TUNEL, with a decrease in the $F4/80^+$ macrophage population. These results suggest that NMN administration enhances the resolution of inflammation and protects mice from DSS-induced colitis.

The description of the present disclosure described above is for illustrative purposes only, and those skilled in the art to which the present disclosure pertains will understand that it can be easily modified into other specific forms without changing the technical spirit or essential characteristics of the present disclosure. Therefore, the embodiments described above should be understood as illustrative in all respects and not limiting.

The scope of the present disclosure is indicated by the following claims, and all changes or modifications derived from the meaning and scope of the claims and equivalent concepts should be interpreted as being included in the scope of the present disclosure.

What is claimed is:

1. A method for treating colitis, comprising administering a pharmaceutical composition comprising nicotinamide mononucleotide (NMN) as an active ingredient to a subject in need of treating the colitis,
    wherein the colitis is caused by nicotinamide phosphoribosyltransferase (NAMPT) protein knock out.

2. The method of claim 1, wherein the NAMPT protein knock out is a knock out of NAMPT in macrophages.

3. The method of claim 1, wherein the subject has low expression level or no expression of NAMPT protein in macrophages.

4. A method for treating colitis, comprising administering a health functional food composition comprising nicotinamide mononucleotide (NMN) as an active ingredient to a subject in need of treating the colitis,
    wherein the colitis is caused by nicotinamide phosphoribosyltransferase (NAMPT) protein knock out.

5. The method of claim 4, wherein the NAMPT protein knock out is a knock out of NAMPT in macrophages.

6. The method of claim 4, wherein the subject has low expression level or no expression of NAMPT protein in macrophages.

* * * * *